[54] RESHAPED MONOCLONAL ANTIBODIES AGAINST AN IMMUNOGLOBULIN ISOTYPE

[75] Inventors: Norman Hardman, Riehen, Switzerland; Frank Kolbinger, Freiburg, Germany; José Saldanha, Enfield, United Kingdom

[73] Assignees: Novartis Corporation, Summit, N.J.; Tanox Biosystems, Inc., Houston, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/127,721

[22] Filed: Sep. 27, 1993

Related U.S. Application Data

[63] Continuation-in-part of application No. 07/952,802, Sep. 25, 1992, abandoned.

[51] Int. Cl.$^7$ .......................... C07K 16/00; C12P 21/08; C07H 21/04; C12N 5/06
[52] U.S. Cl. ..................... 530/387.2; 530/387.3; 530/388.1; 530/388.15; 536/23.53; 435/327; 435/326
[58] Field of Search ...................... 536/23.53; 435/70.21, 435/240.27, 172.2, 240.2, 320.1, 325, 326, 327; 530/387.2, 388.1, 388.15

[56] References Cited

U.S. PATENT DOCUMENTS

| | | |
|---|---|---|
| 5,180,805 | 1/1993 | Gould et al. . |
| 5,420,251 | 5/1995 | Chang . |
| 5,422,258 | 6/1995 | Chang . |
| 5,428,133 | 6/1995 | Chang . |

FOREIGN PATENT DOCUMENTS

| | | |
|---|---|---|
| 0239400 | 9/1987 | European Pat. Off. . |
| 0396505 | 11/1990 | European Pat. Off. . |
| 0438310 | 7/1991 | European Pat. Off. . |
| 0476226 | 3/1992 | European Pat. Off. . |
| 8906138 | 7/1989 | WIPO . |
| 9007861 | 7/1990 | WIPO . |
| 9101991 | 2/1991 | WIPO . |
| 9109967 | 7/1991 | WIPO . |
| 9217207 | 10/1992 | WIPO . |
| 9222653 | 12/1992 | WIPO . |
| 9304173 | 3/1993 | WIPO . |

OTHER PUBLICATIONS

Queen et al, A Humanized Antibody That Binds to the Interleukin 2 Receptor, Proc. Natl. Acad. Sci. USA 86, pp. 10029–10033 (1989).
Kettleborough et al, Humanization of a Mouse Monoclonal Antibody by CDR–Grafting: The Importance of Framework Residues on Loop Conformation, Protein Engineering 4, pp. 773–83(1991).
Chothia et al, Canonical Structures for the Hypervariable Regions of Immunoglobulins, J. Mol. Biol. 196, pp. 901–917 (1987).
Chothia et al, Conformations of Immunoglobulin Hypervariable Regions, Nature 342, pp. 877–883 (1989).
Jonsson et al, Real–Time Biospecific Interaction Analysis Using Surface Plasmon Resonance and a Sensor Chip Technology, BioTechniques 11, pp. 620–627 (1991).
Dersimonian et al, Relationship of Human Variable Region Heavy Chain Germ–Line Genes to Genes Encoding Anti–DNA Autoantibodies, J. Immunology 139, pp. 2496–2501(1987).
Beatty et al, Measurement of Monoclonal Antibody Affinity by Non–Competitive Enzyme Immunoassay J. Immunological Methods 100, pp. 173–179(1987).
Amit et al, Three–Dimensional Structure of an Antigen–Antibody Complex at 2.8A Resolution, Science 233, pp. 747–753 (1986).
Padlan et al, Structure of an Antibody–Antigen Complex: Crystal Structure of the Hyhel–10 Fab–Lysozyme Complex, Proc. Natl. Acad. Sci. USA 86, pp. 5938–5942 (1989).
Newkirk et al, Complete Protein Sequences of the Variable Regions of the Cloned Heavy and Light Chains of a Human Anti–Cytomegalovirus Antibody Reveal a Striking Similarity to Human Monoclonal Rheumatoid Factors of the WA Idiotypic Family, J. Clin. Invest. 81, pp. 1511–1518 (1988).
Kozak, At Least Six Nucleotides Preceding the AUG Initiator Codon Enhance Translation in Mammalian Cells, J. Mol. Biol. 196, pp. 947–950 (1987).
Sheriff et al, Three–Dimensional Structure of an Antibody–Antigen Complex, Proc. Natl. Acad. Sci. USA 84, pp. 8075–8079 (1987).
Furey et al, Structure of a Novel Bence–Jones Protein (Rhe) Fragment at 1.6 A Resolution, J. Mol. Biol. 167, pp. 661–692 (1983).
Breathnach et al, Ovalbumin Gene: Evidence for a Leader Sequence in mRNA and DNA Sequences at the Exon–Intron Boundaries, Proc. Natl. Acad. Sci USA 75, pp. 4853–4857(1978).
Sun et al, Expression of a Mouse/Human Chimeric IgE, J. Cell Biol. 109, 1573(1989).
Kolbinger et al, A Humanized Antibody for the Treatment of Allergy, Poster, Miami, Jan., 1993.
Tempest et al, Reshaping a Human Monoclonal Antibody to Inhibit Human Respiratory Syncytial Virus Infection In Vivo, Bio/Technology 9, pp. 266–271 (1991).
Rousseaux–Prevost ,et al, Studies of the IgE Binding Sites to Rat Mast Cell Receptor with Proteolytic Fragments and with a Monoclonal Antibody Directed Against Epsilon Heavy Chain: Evidence That the Combining Sites are Located in the C,3 Domain, Molecular Immunology 24, pp. 187–196 (1987).

(List continued on next page.)

*Primary Examiner*—Paula K. Hutzell
*Assistant Examiner*—Timothy A. Worrall
*Attorney, Agent, or Firm*—Gregory D. Ferrar

[57] ABSTRACT

The invention relates to reshaped human monoclonal antibodies directed against isotypic determinants of immunoglobulin E (IgE), direct equivalents and derivatives of said antibodies. The molecules of the invention are useful for diagnostics, prophylaxis and treatment of allergy.

10 Claims, 1 Drawing Sheet

OTHER PUBLICATIONS

Baniyash et al, Inhibition of IgE Binding to Mast Cells and Basophils by Monolconal Antibodies to Murine IgE, Eur. J. Immunol. 14, pp. 799–807(1984).

Vercelli et al, The B–Cell Binding Site on Human Immunoglobulin E, Nature 338, pp. 649–651 (1989).

Nissim et al, Localization of the FC ERI Binding Site to the Third Constant Domain of IgE, Int. Arch. Allergy Appl. Immunol. 94, pp. 93–95 (1991).

Helm et al, The Mast Cell Binding Site on Human Immunoglobulin E, Nature 331, pp. 180–183(1988).

Chang et al, Monoclonal Antibodies Specific for Human IgE–Producing B Cells: A Potential Therapeutic for IgE–Mediated Allergic Diseases, Bio/Technology 8, pp. 122–127(1990).

Bourgeois et al, Monoclonal Antibodies to Human IgE: Utilization for Total IgE Quantification and Estimation of Allergen Specific IgE Antibodies, Develop. Biol. Standard 57, pp. 371–379 (1984).

Ichimori et al, Establishment of Hybridomas Secreting Monoclonal Antibodies Against CE2 and CE4 Domains of Human IgE, Hybridoma 4, pp. 47–53 (1985).

Chretien et al, A Monoclonal Anti–IgE Antibody Against an Epitope (Amino Acids 367–376) in the CH3 Domain Inhibits IgE Binding to the Low Affinity IgE Receptor (CD23), J. Immunology 141, pp. 3128–3134 (1988).

Noro et al, Monoclonal Antibody (H107) Inhibiting IgE Binding to FCER(+) Human Lymphocytes, J. Immunology 137, pp. 1258–1263 (1986).

Kings et al, Histamine Release from Human Leukocytes by Anti–IgE Antibodies: Influence of Multiple or Single Epitope Recognition, Diagnostic Immunology 4, pp. 89–96(1986).

Grassi et al, Quantitative Determination of Total and Specific Human IgE with the Use of Monoclonal Antibodies, J. Allergy Clin. Immunology 77, pp. 808–822 (1986).

Haba et al, Production of Syngeneic Autoreactive Monoclonal Antibodies Specific for Isotypic Determinants of IgE, J. Immunological Methods, 105, pp. 193–199(1987).

Baniyash et al, Relationships Between Epitopes on IgE Recognized by Defined Monoclonal Antibodies and By the $FC_E$ Receptor on Basophils, J. Immunology 136, pp. 588–593(1986).

Baniyash et al, Anti–IgE Monoclonal Antibodies Directed at the $FC_E$ Receptor Binding Site, Molecular Immunology 25, pp. 705–711 (1988).

Nakajima et al, Effect of Anti–IgE Antibodies on IgE Binding to CD23, Allergy 44, pp. 187–191 (1989).

Hook et al, Monoclonal Antibodies to Human IgE, Fed. Proc. 10, p. 968 (Abstr. 4177) (1981).

Lewis et al; Immunoglobulin Complementarity–Determining Region Grafting by Recombinant Polymerase Chain Reaction to Generate Humanized Monoclonal Antibodies; Gene 101 (1991) 297–302.

Kolbinger et al; A Humanized Antibody for the Treatment of Allergy Protein Engineering vol.6, Suppl. 1993 p. 90.

Riechmann et al; Reshaping Human Antibodies for Therapy Nature vol. 332, Mar. 24, 1988, pp. 323–327.

Heussler et al; New Concepts of IgE Regulation; Int Arch Allergy Appl Immunol, 1991; 94:87–90.

RudiKoff et al., PNAS USA 79:1979–1983, 1982.

Liou et al. Faseb J 5–A1670, Mar. 19, 1991.

SEQUENCE LISTING

```
(1) GENERAL INFORMATION:

(iii) NUMBER OF SEQUENCES: 55

(2) INFORMATION FOR SEQ ID NO:1:

(i) SEQUENCE CHARACTERISTICS:
```

(A) LENGTH: 370 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 1..369
            (D) OTHER INFORMATION: /product= "heavy chain variable
                domain of antibody TES-C21"

(xi) SEQUENCE DESCRIPTION: SEQ ID NO:1:

```
CAG GTT CAG TTG CAG CAG TCT GGA GCG GAG CTG ATG AAG CCT GGG GCC        48
Gln Val Gln Leu Gln Gln Ser Gly Ala Glu Leu Met Lys Pro Gly Ala
 1               5                  10                  15

TCA GTG AAG ATC TCC TGC AAG ACT ACT GGC TAC ACA TTC AGT ATG TAC        96
Ser Val Lys Ile Ser Cys Lys Thr Thr Gly Tyr Thr Phe Ser Met Tyr
             20                  25                  30

TGG TTA GAG TGG GTA AAG CAG AGG CCT GGA CAT GGC CTT GAG TGG GTT       144
Trp Leu Glu Trp Val Lys Gln Arg Pro Gly His Gly Leu Glu Trp Val
         35                  40                  45

GGA GAG ATT TCA CCT GGA ACT TTT ACT ACT AAC TAC AAT GAG AAA TTC       192
Gly Glu Ile Ser Pro Gly Thr Phe Thr Thr Asn Tyr Asn Glu Lys Phe
 50                  55                  60

AAG GCC AAG GCC ACA TTC ACT GCG GAT ACA TCC TCC AAC ACA GCC TAC       240
Lys Ala Lys Ala Thr Phe Thr Ala Asp Thr Ser Ser Asn Thr Ala Tyr
 65                  70                  75                  80

CTG CAA CTC AGC GGC CTG ACA TCT GAG GAC TCT GCC GTC TAC TTC TGT       288
Leu Gln Leu Ser Gly Leu Thr Ser Glu Asp Ser Ala Val Tyr Phe Cys
             85                  90                  95

GCA AGA TTC TCC CAT TTT TCC GGT AGT AAC TAC GAC TAC TTT GAC TAC       336
Ala Arg Phe Ser His Phe Ser Gly Ser Asn Tyr Asp Tyr Phe Asp Tyr
            100                 105                 110

TGG GGC CAG GGC ACC TCT CTC ACA GTC TCC TCC G                         370
Trp Gly Gln Gly Thr Ser Leu Thr Val Ser Ser
        115                 120
```

(2) INFORMATION FOR SEQ ID NO:2:

(i) SEQUENCE CHARACTERISTICS:
            (A) LENGTH: 123 amino acids
            (B) TYPE: amino acid
            (D) TOPOLOGY: linear (ii) MOLECULE TYPE: protein (xi) SEQUENCE DESCRIPTION: SEQ ID NO:2:

```
Gln Val Gln Leu Gln Gln Ser Gly Ala Glu Leu Met Lys Pro Gly Ala
 1               5                  10                  15

Ser Val Lys Ile Ser Cys Lys Thr Thr Gly Tyr Thr Phe Ser Met Tyr
             20                  25                  30

Trp Leu Glu Trp Val Lys Gln Arg Pro Gly His Gly Leu Glu Trp Val
         35                  40                  45

Gly Glu Ile Ser Pro Gly Thr Phe Thr Thr Asn Tyr Asn Glu Lys Phe
 50                  55                  60

Lys Ala Lys Ala Thr Phe Thr Ala Asp Thr Ser Ser Asn Thr Ala Tyr
 65                  70                  75                  80

Leu Gln Leu Ser Gly Leu Thr Ser Glu Asp Ser Ala Val Tyr Phe Cys
             85                  90                  95

Ala Arg Phe Ser His Phe Ser Gly Ser Asn Tyr Asp Tyr Phe Asp Tyr
            100                 105                 110
```

(2) INFORMATION FOR SEQ ID NO:3:

(i) SEQUENCE CHARACTERISTICS:
        (A) LENGTH: 322 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..321
        (D) OTHER INFORMATION: /product= "light chain variable
            domain of murine antibody TES-C21"

(xi) SEQUENCE DESCRIPTION: SEQ ID NO:3:

```
GAC ATC TTG CTG ACT CAG TCT CCA GCC ATC CTG TCT GTG AGT CCA GGA      48
Asp Ile Leu Leu Thr Gln Ser Pro Ala Ile Leu Ser Val Ser Pro Gly
 1               5                  10                  15

GAA AGA GTC AGT TTC TCC TGC AGG GCC AGT CAG AGC ATT GGC ACA AAC      96
Glu Arg Val Ser Phe Ser Cys Arg Ala Ser Gln Ser Ile Gly Thr Asn
                20                  25                  30

ATA CAC TGG TAT CAG CAA AGA ACA GAT GGT TCT CCA AGG CTT CTC ATA     144
Ile His Trp Tyr Gln Gln Arg Thr Asp Gly Ser Pro Arg Leu Leu Ile
            35                  40                  45

AAG TAT GCT TCT GAG TCT ATC TCT GGG ATC CCT TCC AGG TTT AGT GGC     192
Lys Tyr Ala Ser Glu Ser Ile Ser Gly Ile Pro Ser Arg Phe Ser Gly
    50                  55                  60

AGT GGA TCA GGG ACA GAG TTT ACT CTA AAC ATC AAC AGT GTG GAG TCT     240
Ser Gly Ser Gly Thr Glu Phe Thr Leu Asn Ile Asn Ser Val Glu Ser
65                  70                  75                  80

GAA GAT ATT GCA GAT TAT TAC TGT CAA CAA AGT GAT AGC TGG CCA ACC     288
Glu Asp Ile Ala Asp Tyr Tyr Cys Gln Gln Ser Asp Ser Trp Pro Thr
                85                  90                  95

ACG TTC GGA GGG GGG ACC AAG CTG GAG ATA AAA C                       322
Thr Phe Gly Gly Gly Thr Lys Leu Glu Ile Lys
                100                 105
```

(2) INFORMATION FOR SEQ ID NO:4:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:4:

```
Asp Ile Leu Leu Thr Gln Ser Pro Ala Ile Leu Ser Val Ser Pro Gly
 1               5                  10                  15

Glu Arg Val Ser Phe Ser Cys Arg Ala Ser Gln Ser Ile Gly Thr Asn
                20                  25                  30

Ile His Trp Tyr Gln Gln Arg Thr Asp Gly Ser Pro Arg Leu Leu Ile
            35                  40                  45

Lys Tyr Ala Ser Glu Ser Ile Ser Gly Ile Pro Ser Arg Phe Ser Gly
    50                  55                  60

Ser Gly Ser Gly Thr Glu Phe Thr Leu Asn Ile Asn Ser Val Glu Ser
65                  70                  75                  80

Glu Asp Ile Ala Asp Tyr Tyr Cys Gln Gln Ser Asp Ser Trp Pro Thr
```

85                  90                  95
Thr Phe Gly Gly Gly Thr Lys Leu Glu Ile Lys
                    100                 105

(2) INFORMATION FOR SEQ ID NO:5:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 22..402

(ix) FEATURE:
        (A) NAME/KEY: mat_peptide
        (B) LOCATION: 82..402
        (D) OTHER INFORMATION: /product= "light chain variable
            region C21-L1"

(xi) SEQUENCE DESCRIPTION: SEQ ID NO:5:

```
CTCCGCAAGC TTGCCGCCAC C ATG GAG ACC CCC GCC CAG CTG CTG TTC CTG          51
                         Met Glu Thr Pro Ala Gln Leu Leu Phe Leu
                         -20                 -15

CTG CTG CTG TGG CTG CCC GAC ACC ACC GGC GAC ATC CTG CTG ACC CAG          99
Leu Leu Leu Trp Leu Pro Asp Thr Thr Gly Asp Ile Leu Leu Thr Gln
-10                 -5                  1               5

AGC CCC GGC ACC CTG AGC CTG AGC CCC GGC GAG AGG GCC ACC CTG AGC         147
Ser Pro Gly Thr Leu Ser Leu Ser Pro Gly Glu Arg Ala Thr Leu Ser
                10                  15                  20

TGC AGG GCC AGC CAG AGC ATC GGC ACC AAC ATC CAC TGG TAC CAG CAG         195
Cys Arg Ala Ser Gln Ser Ile Gly Thr Asn Ile His Trp Tyr Gln Gln
        25                  30                  35

AAG CCC GGC CAG GCC CCC AGG CTG CTG ATC AAG TAC GCC AGC GAG AGC         243
Lys Pro Gly Gln Ala Pro Arg Leu Leu Ile Lys Tyr Ala Ser Glu Ser
    40                  45                  50

ATC AGC GGC ATC CCC AGC AGG TTC AGC GGC AGC GGC AGC GGC ACC GAC         291
Ile Ser Gly Ile Pro Ser Arg Phe Ser Gly Ser Gly Ser Gly Thr Asp
55                  60                  65                  70

TTC ACC CTG ACC ATC AGC AGG CTG GAG CCC GAG GAC TTC GCC ATG TAC         339
Phe Thr Leu Thr Ile Ser Arg Leu Glu Pro Glu Asp Phe Ala Met Tyr
                75                  80                  85

TAC TGC CAG CAG AGC GAC AGC TGG CCC ACC ACC TTC GGC CAG GGC ACC         387
Tyr Cys Gln Gln Ser Asp Ser Trp Pro Thr Thr Phe Gly Gln Gly Thr
            90                  95                 100

AAG GTG GAG ATC AAA CGTGAGTATT CTAGAAGGAT CC                            424
Lys Val Glu Ile Lys
        105
```

(2) INFORMATION FOR SEQ ID NO:6:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO:6:

Met Glu Thr Pro Ala Gln Leu Leu Phe Leu Leu Leu Leu Trp Leu Pro
-20                 -15                 -10                 -5

```
Asp Thr Thr Gly Asp Ile Leu Leu Thr Gln Ser Pro Gly Thr Leu Ser
              1               5                  10
Leu Ser Pro Gly Glu Arg Ala Thr Leu Ser Cys Arg Ala Ser Gln Ser
         15                  20                  25
Ile Gly Thr Asn Ile His Trp Tyr Gln Gln Lys Pro Gly Gln Ala Pro
         30                  35                  40
Arg Leu Leu Ile Lys Tyr Ala Ser Glu Ser Ile Ser Gly Ile Pro Ser
 45                  50                  55                  60
Arg Phe Ser Gly Ser Gly Ser Gly Thr Asp Phe Thr Leu Thr Ile Ser
                 65                  70                  75
Arg Leu Glu Pro Glu Asp Phe Ala Met Tyr Tyr Cys Gln Gln Ser Asp
                 80                  85                  90
Ser Trp Pro Thr Thr Phe Gly Gln Gly Thr Lys Val Glu Ile Lys
         95                 100                 105
```

(2) INFORMATION FOR SEQ ID NO:7:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 22..402

(ix) FEATURE:
        (A) NAME/KEY: mat_peptide
        (B) LOCATION: 82..402
        (D) OTHER INFORMATION: /product= "light chain variable
            region C21-L2"

(xi) SEQUENCE DESCRIPTION: SEQ ID NO:7:

```
CTCCGCAAGC TTGCCGCCAC C ATG GAG ACC CCC GCC CAG CTG CTG TTC CTG         51
                       Met Glu Thr Pro Ala Gln Leu Leu Phe Leu
                       -20                 -15

CTG CTG CTG TGG CTG CCC GAC ACC ACC GGC GAC ATC CTG CTG ACC CAG         99
Leu Leu Leu Trp Leu Pro Asp Thr Thr Gly Asp Ile Leu Leu Thr Gln
-10                 -5                  1               5

AGC CCC GGC ACC CTG AGC CTG AGC CCC GGC GAG AGG GCC ACC CTG AGC        147
Ser Pro Gly Thr Leu Ser Leu Ser Pro Gly Glu Arg Ala Thr Leu Ser
            10                  15                  20

TGC AGG GCC AGC CAG AGC ATC GGC ACC AAC ATC CAC TGG TAC CAG CAG        195
Cys Arg Ala Ser Gln Ser Ile Gly Thr Asn Ile His Trp Tyr Gln Gln
             25                  30                  35

AAG CCC GGC CAG GCC CCC AGG CTG CTG ATC AAG TAC GCC AGC GAG AGC        243
Lys Pro Gly Gln Ala Pro Arg Leu Leu Ile Lys Tyr Ala Ser Glu Ser
 40                  45                  50

ATC AGC GGC ATC CCC GAC AGG TTC AGC GGC AGC GGC AGC GGC ACC GAC        291
Ile Ser Gly Ile Pro Asp Arg Phe Ser Gly Ser Gly Ser Gly Thr Asp
 55                  60                  65                  70

TTC ACC CTG ACC ATC AGC AGG CTG GAG CCC GAG GAC TTC GCC ATG TAC        339
Phe Thr Leu Thr Ile Ser Arg Leu Glu Pro Glu Asp Phe Ala Met Tyr
                 75                  80                  85

TAC TGC CAG CAG AGC GAC AGC TGG CCC ACC ACC TTC GGC CAG GGC ACC        387
Tyr Cys Gln Gln Ser Asp Ser Trp Pro Thr Thr Phe Gly Gln Gly Thr
             90                  95                 100

AAG GTG GAG ATC AAA CGTGAGTATT CTAGAAGGAT CC                           424
Lys Val Glu Ile Lys
         105
```

(2) INFORMATION FOR SEQ ID NO:8:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO:8:

```
Met Glu Thr Pro Ala Gln Leu Leu Phe Leu Leu Leu Trp Leu Pro
-20             -15                 -10                 -5

Asp Thr Thr Gly Asp Ile Leu Leu Thr Gln Ser Pro Gly Thr Leu Ser
              1                 5                  10

Leu Ser Pro Gly Glu Arg Ala Thr Leu Ser Cys Arg Ala Ser Gln Ser
         15                  20                  25

Ile Gly Thr Asn Ile His Trp Tyr Gln Gln Lys Pro Gly Gln Ala Pro
     30                  35                  40

Arg Leu Leu Ile Lys Tyr Ala Ser Glu Ser Ile Ser Gly Ile Pro Asp
 45                  50                  55                  60

Arg Phe Ser Gly Ser Gly Ser Gly Thr Asp Phe Thr Leu Thr Ile Ser
             65                  70                  75

Arg Leu Glu Pro Glu Asp Phe Ala Met Tyr Tyr Cys Gln Gln Ser Asp
         80                  85                  90

Ser Trp Pro Thr Thr Phe Gly Gln Gly Thr Lys Val Glu Ile Lys
         95                 100                 105
```

(2) INFORMATION FOR SEQ ID NO:9:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 22..402

(ix) FEATURE:
        (A) NAME/KEY: mat_peptide
        (B) LOCATION: 82..402
        (D) OTHER INFORMATION: /product= "light chain variable
            region C21-L3"

(xi) SEQUENCE DESCRIPTION: SEQ ID NO:9:

```
CTCCGCAAGC TTGCCGCCAC C ATG GAG ACC CCC GCC CAG CTG CTG TTC CTG        51
                         Met Glu Thr Pro Ala Gln Leu Leu Phe Leu
                         -20                 -15

CTG CTG CTG TGG CTG CCC GAC ACC ACC GGC GAG ATC GTG CTG ACC CAG        99
Leu Leu Leu Trp Leu Pro Asp Thr Thr Gly Glu Ile Val Leu Thr Gln
-10                 -5                   1                   5

AGC CCC GGC ACC CTG AGC CTG AGC CCC GGC GAG AGG GCC ACC CTG AGC       147
Ser Pro Gly Thr Leu Ser Leu Ser Pro Gly Glu Arg Ala Thr Leu Ser
             10                  15                  20

TGC AGG GCC AGC CAG AGC ATC GGC ACC AAC ATC CAC TGG TAC CAG CAG       195
Cys Arg Ala Ser Gln Ser Ile Gly Thr Asn Ile His Trp Tyr Gln Gln
         25                  30                  35

AAG CCC GGC CAG GCC CCC AGG CTG CTG ATC AAG TAC GCC AGC GAG AGC       243
Lys Pro Gly Gln Ala Pro Arg Leu Leu Ile Lys Tyr Ala Ser Glu Ser
     40                  45                  50
```

```
ATC AGC GGC ATC CCC AGC AGG TTC AGC GGC AGC GGC AGC GGC ACC GAC          291
Ile Ser Gly Ile Pro Ser Arg Phe Ser Gly Ser Gly Ser Gly Thr Asp
 55              60                  65                  70

TTC ACC CTG ACC ATC AGC AGG CTG GAG CCC GAG GAC TTC GCC ATG TAC          339
Phe Thr Leu Thr Ile Ser Arg Leu Glu Pro Glu Asp Phe Ala Met Tyr
                 75                  80                  85

TAC TGC CAG CAG AGC GAC AGC TGG CCC ACC ACC TTC GGC CAG GGC ACC          387
Tyr Cys Gln Gln Ser Asp Ser Trp Pro Thr Thr Phe Gly Gln Gly Thr
             90                  95                 100

AAG GTG GAG ATC AAA CGTGAGTATT CTAGAAGGAT CC                             424
Lys Val Glu Ile Lys
            105

(2) INFORMATION FOR SEQ ID NO:10:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO:10:

Met Glu Thr Pro Ala Gln Leu Leu Phe Leu Leu Leu Leu Trp Leu Pro
-20                 -15                 -10                  -5

Asp Thr Thr Gly Glu Ile Val Leu Thr Gln Ser Pro Gly Thr Leu Ser
                 1                   5                  10

Leu Ser Pro Gly Glu Arg Ala Thr Leu Ser Cys Arg Ala Ser Gln Ser
             15                  20                  25

Ile Gly Thr Asn Ile His Trp Tyr Gln Gln Lys Pro Gly Gln Ala Pro
         30                  35                  40

Arg Leu Leu Ile Lys Tyr Ala Ser Glu Ser Ile Ser Gly Ile Pro Ser
 45                  50                  55                  60

Arg Phe Ser Gly Ser Gly Ser Gly Thr Asp Phe Thr Leu Thr Ile Ser
             65                  70                  75

Arg Leu Glu Pro Glu Asp Phe Ala Met Tyr Tyr Cys Gln Gln Ser Asp
         80                  85                  90

Ser Trp Pro Thr Thr Phe Gly Gln Gly Thr Lys Val Glu Ile Lys
     95                 100                 105

(2) INFORMATION FOR SEQ ID NO:11:

(i) SEQUENCE CHARACTERISTICS:
        (A) LENGTH: 468 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 22..447

(ix) FEATURE:
        (A) NAME/KEY: mat_peptide
        (B) LOCATION: 79..447
        (D) OTHER INFORMATION: /product= "heavy chain variable
            region C21-H1"

(xi) SEQUENCE DESCRIPTION: SEQ ID NO:11:

CTCCGCAAGC TTGCCGCCAC C ATG GAC TGG ACC TGG AGG GTG TTC TGC CTG         51
                         Met Asp Trp Thr Trp Arg Val Phe Cys Leu
                         -19             -15                 -10
```

```
CTG GCC GTG GCC CCC GGC GCC CAC AGC CAG GTG CAG CTG GTG CAG AGC        99
Leu Ala Val Ala Pro Gly Ala His Ser Gln Val Gln Leu Val Gln Ser
            -5              1               5

GGC GCC GAG GTG AAG AAG CCC GGC GCC AGC GTG AAG GTG AGC TGC AAG       147
Gly Ala Glu Val Lys Lys Pro Gly Ala Ser Val Lys Val Ser Cys Lys
        10              15              20

GCC AGC GGC TAC ACC TTC AGC ATG TAC TGG CTG GAG TGG GTG AAG CAG       195
Ala Ser Gly Tyr Thr Phe Ser Met Tyr Trp Leu Glu Trp Val Lys Gln
25              30              35

AGG CCC GGC CAC GGC CTG GAG TGG GTG GGC GAG ATC AGC CCC GGC ACC       243
Arg Pro Gly His Gly Leu Glu Trp Val Gly Glu Ile Ser Pro Gly Thr
40              45              50              55

TTC ACC ACC AAC TAC AAC GAG AAG TTC AAG GCC AAG GCC ACC TTC ACC       291
Phe Thr Thr Asn Tyr Asn Glu Lys Phe Lys Ala Lys Ala Thr Phe Thr
            60              65              70

GCC GAC ACC AGC ACC AAC ACC GCC TAC ATG GAG CTG AGC AGC CTG ACC       339
Ala Asp Thr Ser Thr Asn Thr Ala Tyr Met Glu Leu Ser Ser Leu Thr
            75              80              85

AGC GAG GAC ACC GCC GTG TAC TAC TGC GCC AGG TTC AGC CAC TTC AGC       387
Ser Glu Asp Thr Ala Val Tyr Tyr Cys Ala Arg Phe Ser His Phe Ser
        90              95              100

GGC AGC AAC TAC GAC TAC TTC GAC TAC TGG GGC CAG GGC ACC CTG GTG       435
Gly Ser Asn Tyr Asp Tyr Phe Asp Tyr Trp Gly Gln Gly Thr Leu Val
105             110             115

ACC GTG AGC TCA GGTGAGTTCT AGAAGGGATC C                               468
Thr Val Ser Ser
120
```

(2) INFORMATION FOR SEQ ID NO:12:

(i) SEQUENCE CHARACTERISTICS:
        (A) LENGTH: 142 amino acids
        (B) TYPE: amino acid
        (D) TOPOLOGY: linear (ii) MOLECULE TYPE: protein (xi) SEQUENCE DESCRIPTION: SEQ ID NO:12:

```
Met Asp Trp Thr Trp Arg Val Phe Cys Leu Leu Ala Val Ala Pro Gly
-19             -15             -10                     -5

Ala His Ser Gln Val Gln Leu Val Gln Ser Gly Ala Glu Val Lys Lys
            1               5               10

Pro Gly Ala Ser Val Lys Val Ser Cys Lys Ala Ser Gly Tyr Thr Phe
        15              20              25

Ser Met Tyr Trp Leu Glu Trp Val Lys Gln Arg Pro Gly His Gly Leu
30              35              40              45

Glu Trp Val Gly Glu Ile Ser Pro Gly Thr Phe Thr Thr Asn Tyr Asn
            50              55              60

Glu Lys Phe Lys Ala Lys Ala Thr Phe Thr Ala Asp Thr Ser Thr Asn
            65              70              75

Thr Ala Tyr Met Glu Leu Ser Ser Leu Thr Ser Glu Asp Thr Ala Val
            80              85              90

Tyr Tyr Cys Ala Arg Phe Ser His Phe Ser Gly Ser Asn Tyr Asp Tyr
        95              100             105

Phe Asp Tyr Trp Gly Gln Gly Thr Leu Val Thr Val Ser Ser
110             115             120
```

(2) INFORMATION FOR SEQ ID NO:13:

(i) SEQUENCE CHARACTERISTICS:
  (A) LENGTH: 468 base pairs
  (B) TYPE: nucleic acid
  (C) STRANDEDNESS: double
  (D) TOPOLOGY: linear (ii) MOLECULE TYPE: DNA (genomic)

(ix) FEATURE:
  (A) NAME/KEY: CDS
  (B) LOCATION: 22..447

(ix) FEATURE:
  (A) NAME/KEY: mat_peptide
  (B) LOCATION: 79..447
  (D) OTHER INFORMATION: /product= "heavy chain variable region C21-H3"

(xi) SEQUENCE DESCRIPTION: SEQ ID NO:13:

```
CTCCGCAAGC TTGCCGCCAC C ATG GAC TGG ACC TGG AGG GTG TTC TGC CTG        51
                        Met Asp Trp Thr Trp Arg Val Phe Cys Leu
                        -19             -15                 -10

CTG GCC GTG GCC CCC GGC GCC CAC AGC CAG GTG CAG CTG GTG CAG AGC        99
Leu Ala Val Ala Pro Gly Ala His Ser Gln Val Gln Leu Val Gln Ser
              -5                  1               5

GGC GCC GAG GTG AAG AAG CCC GGC GCC AGC GTG AAG GTG AGC TGC AAG       147
Gly Ala Glu Val Lys Lys Pro Gly Ala Ser Val Lys Val Ser Cys Lys
        10              15                  20

GCC AGC GGC TAC ACC TTC AGC ATG TAC TGG CTG GAG TGG GTG AGG CAG       195
Ala Ser Gly Tyr Thr Phe Ser Met Tyr Trp Leu Glu Trp Val Arg Gln
25                  30                  35

GCC CCC GGC CAC GGC CTG GAG TGG GTG GGC GAG ATC AGC CCC GGC ACC       243
Ala Pro Gly His Gly Leu Glu Trp Val Gly Glu Ile Ser Pro Gly Thr
40                  45                  50                  55

TTC ACC ACC AAC TAC AAC GAG AAG TTC AAG GCC AGG GCC ACC TTC ACC       291
Phe Thr Thr Asn Tyr Asn Glu Lys Phe Lys Ala Arg Ala Thr Phe Thr
                60                  65                  70

GCC GAC ACC AGC ACC AAC ACC GCC TAC ATG GAG CTG AGC AGC CTG AGG       339
Ala Asp Thr Ser Thr Asn Thr Ala Tyr Met Glu Leu Ser Ser Leu Arg
            75                  80                  85

AGC GAG GAC ACC GCC GTG TAC TAC TGC GCC AGG TTC AGC CAC TTC AGC       387
Ser Glu Asp Thr Ala Val Tyr Tyr Cys Ala Arg Phe Ser His Phe Ser
        90                  95                  100

GGC AGC AAC TAC GAC TAC TTC GAC TAC TGG GGC CAG GGC ACC CTG GTG       435
Gly Ser Asn Tyr Asp Tyr Phe Asp Tyr Trp Gly Gln Gly Thr Leu Val
105                 110                 115

ACC GTG AGC TCA GGTGAGTTCT AGAAGGGATC C                               468
Thr Val Ser Ser
120
```

(2) INFORMATION FOR SEQ ID NO:14:

(i) SEQUENCE CHARACTERISTICS:
  (A) LENGTH: 142 amino acids
  (B) TYPE: amino acid
  (D) TOPOLOGY: linear (ii) MOLECULE TYPE: protein (xi) SEQUENCE DESCRIPTION: SEQ ID NO:14:

```
Met Asp Trp Thr Trp Arg Val Phe Cys Leu Leu Ala Val Ala Pro Gly
-19             -15                 -10                 -5

Ala His Ser Gln Val Gln Leu Val Gln Ser Gly Ala Glu Val Lys Lys
            1               5                   10

Pro Gly Ala Ser Val Lys Val Ser Cys Lys Ala Ser Gly Tyr Thr Phe
```

```
                 15                  20                  25
Ser Met Tyr Trp Leu Glu Trp Val Arg Gln Ala Pro Gly His Gly Leu
 30                  35                  40                  45

Glu Trp Val Gly Glu Ile Ser Pro Gly Thr Phe Thr Thr Asn Tyr Asn
                 50                  55                  60

Glu Lys Phe Lys Ala Arg Ala Thr Phe Thr Ala Asp Thr Ser Thr Asn
             65                  70                  75

Thr Ala Tyr Met Glu Leu Ser Ser Leu Arg Ser Glu Asp Thr Ala Val
         80                  85                  90

Tyr Tyr Cys Ala Arg Phe Ser His Phe Ser Gly Ser Asn Tyr Asp Tyr
     95                  100                 105

Phe Asp Tyr Trp Gly Gln Gly Thr Leu Val Thr Val Ser Ser
110                 115                 120
```

(2) INFORMATION FOR SEQ ID NO:15:

(i) SEQUENCE CHARACTERISTICS:
        (A) LENGTH: 467 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 22..447

(ix) FEATURE:
        (A) NAME/KEY: mat_peptide
        (B) LOCATION: 79..447
        (D) OTHER INFORMATION: /product= "heavy chain variable
            region C21-Hay1"

(xi) SEQUENCE DESCRIPTION: SEQ ID NO:15:

```
CTCCGCAAGC TTGCCGCCAC C ATG GAC TGG ACC TGG AGG GTG TTC TGC CTG        51
                       Met Asp Trp Thr Trp Arg Val Phe Cys Leu
                       -19             -15                 -10

CTG GCC GTG GCC CCC GGC GCC CAC AGC CAG GTG CAG CTG GTG CAG AGC        99
Leu Ala Val Ala Pro Gly Ala His Ser Gln Val Gln Leu Val Gln Ser
                -5                   1               5

GGC GCC GAG GTG AAG AAG CCC GGC GCC AGC GTG AAG GTG AGC TGC AAG       147
Gly Ala Glu Val Lys Lys Pro Gly Ala Ser Val Lys Val Ser Cys Lys
         10                  15                  20

GCC AGC GGC TAC ACC TTC AGC ATG TAC TGG CTG GAG TGG GTG AAG CAG       195
Ala Ser Gly Tyr Thr Phe Ser Met Tyr Trp Leu Glu Trp Val Lys Gln
     25                  30                  35

AGG CCC GGC CAG AGG CTG GAG TGG ATG GGC GAG ATC AGC CCC GGC ACC       243
Arg Pro Gly Gln Arg Leu Glu Trp Met Gly Glu Ile Ser Pro Gly Thr
 40                  45                  50                  55

TTC ACC ACC AAC TAC AAC GAG AAG TTC AAG GCC AAG GCC ACC TTC ACC       291
Phe Thr Thr Asn Tyr Asn Glu Lys Phe Lys Ala Lys Ala Thr Phe Thr
                 60                  65                  70

GCC GAC ACC AGC GCC AGC ACC GCC TAC ATG GAG CTG AGC AGC CTG ACC       339
Ala Asp Thr Ser Ala Ser Thr Ala Tyr Met Glu Leu Ser Ser Leu Thr
             75                  80                  85

AGC GAG GAC ACC GCC GTG TAC TAC TGC GCC AGG TTC AGC CAC TTC AGC       387
Ser Glu Asp Thr Ala Val Tyr Tyr Cys Ala Arg Phe Ser His Phe Ser
         90                  95                 100

GGC AGC AAC TAC GAC TAC TTC GAC TAC TGG GGC CAG GGC ACC CTG GTG       435
Gly Ser Asn Tyr Asp Tyr Phe Asp Tyr Trp Gly Gln Gly Thr Leu Val
    105                 110                 115
```

```
ACC GTG AGC TCA GGTGAGTTCT AGAAGGATCC                                         467
Thr Val Ser Ser
120
```

(2) INFORMATION FOR SEQ ID NO:16:

(i) SEQUENCE CHARACTERISTICS:
        (A) LENGTH: 142 amino acids
        (B) TYPE: amino acid
        (D) TOPOLOGY: linear (ii) MOLECULE TYPE: protein (xi) SEQUENCE DESCRIPTION: SEQ ID NO:16:

```
Met Asp Trp Thr Trp Arg Val Phe Cys Leu Leu Ala Val Ala Pro Gly
-19             -15             -10                 -5

Ala His Ser Gln Val Gln Leu Val Gln Ser Gly Ala Glu Val Lys Lys
            1               5                   10

Pro Gly Ala Ser Val Lys Val Ser Cys Lys Ala Ser Gly Tyr Thr Phe
        15              20                  25

Ser Met Tyr Trp Leu Glu Trp Val Lys Gln Arg Pro Gly Gln Arg Leu
30              35                  40                      45

Glu Trp Met Gly Glu Ile Ser Pro Gly Thr Phe Thr Thr Asn Tyr Asn
                50                  55                  60

Glu Lys Phe Lys Ala Lys Ala Thr Phe Thr Ala Asp Thr Ser Ala Ser
            65                  70                  75

Thr Ala Tyr Met Glu Leu Ser Ser Leu Thr Ser Glu Asp Thr Ala Val
            80                  85                  90

Tyr Tyr Cys Ala Arg Phe Ser His Phe Ser Gly Ser Asn Tyr Asp Tyr
        95                  100                 105

Phe Asp Tyr Trp Gly Gln Gly Thr Leu Val Thr Val Ser Ser
110                 115                 120
```

(2) INFORMATION FOR SEQ ID NO:17:

(i) SEQUENCE CHARACTERISTICS:
        (A) LENGTH: 467 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 22..447

(ix) FEATURE:
        (A) NAME/KEY: mat_peptide
        (B) LOCATION: 79..447
        (D) OTHER INFORMATION: /product= "heavy chain variable
            region C21-Hay3"

(xi) SEQUENCE DESCRIPTION: SEQ ID NO:17:

```
CTCCGCAAGC TTGCCGCCAC C ATG GAC TGG ACC TGG AGG GTG TTC TGC CTG          51
                       Met Asp Trp Thr Trp Arg Val Phe Cys Leu
                       -19             -15                 -10

CTG GCC GTG GCC CCC GGC GCC CAC AGC CAG GTG CAG CTG GTG CAG AGC          99
Leu Ala Val Ala Pro Gly Ala His Ser Gln Val Gln Leu Val Gln Ser
            -5                  1               5

GGC GCC GAG GTG AAG AAG CCC GGC GCC AGC GTG AAG GTG AGC TGC AAG         147
Gly Ala Glu Val Lys Lys Pro Gly Ala Ser Val Lys Val Ser Cys Lys
        10                  15                  20

GCC AGC GGC TAC ACC TTC AGC ATG TAC TGG CTG GAG TGG GTG AGG CAG         195
```

-continued

```
Ala Ser Gly Tyr Thr Phe Ser Met Tyr Trp Leu Glu Trp Val Arg Gln
         25                  30                  35

GCC CCC GGC CAG AGG CTG GAG TGG ATG GGC GAG ATC AGC CCC GGC ACC      243
Ala Pro Gly Gln Arg Leu Glu Trp Met Gly Glu Ile Ser Pro Gly Thr
 40                  45                  50                  55

TTC ACC ACC AAC TAC AAC GAG AAG TTC AAG GCC AGG GCC ACC TTC ACC      291
Phe Thr Thr Asn Tyr Asn Glu Lys Phe Lys Ala Arg Ala Thr Phe Thr
                 60                  65                  70

GCC GAC ACC AGC GCC AGC ACC GCC TAC ATG GAG CTG AGC AGC CTG AGG      339
Ala Asp Thr Ser Ala Ser Thr Ala Tyr Met Glu Leu Ser Ser Leu Arg
             75                  80                  85

AGC GAG GAC ACC GCC GTG TAC TAC TGC GCC AGG TTC AGC CAC TTC AGC      387
Ser Glu Asp Thr Ala Val Tyr Tyr Cys Ala Arg Phe Ser His Phe Ser
         90                  95                 100

GGC AGC AAC TAC GAC TAC TTC GAC TAC TGG GGC CAG GGC ACC CTG GTG      435
Gly Ser Asn Tyr Asp Tyr Phe Asp Tyr Trp Gly Gln Gly Thr Leu Val
105                 110                 115

ACC GTG AGC TCA GGTGAGTTCT AGAAGGATCC                                467
Thr Val Ser Ser
120
```

(2) INFORMATION FOR SEQ ID NO:18:

(i) SEQUENCE CHARACTERISTICS:
        (A) LENGTH: 142 amino acids
        (B) TYPE: amino acid
        (D) TOPOLOGY: linear (ii) MOLECULE TYPE: protein (xi) SEQUENCE DESCRIPTION: SEQ ID NO:18:

```
Met Asp Trp Thr Trp Arg Val Phe Cys Leu Leu Ala Val Ala Pro Gly
-19             -15                 -10                  -5

Ala His Ser Gln Val Gln Leu Val Gln Ser Gly Ala Glu Val Lys Lys
              1                   5                  10

Pro Gly Ala Ser Val Lys Val Ser Cys Lys Ala Ser Gly Tyr Thr Phe
         15                  20                  25

Ser Met Tyr Trp Leu Glu Trp Val Arg Gln Ala Pro Gly Gln Arg Leu
 30                  35                  40                  45

Glu Trp Met Gly Glu Ile Ser Pro Gly Thr Phe Thr Thr Asn Tyr Asn
                 50                  55                  60

Glu Lys Phe Lys Ala Arg Ala Thr Phe Thr Ala Asp Thr Ser Ala Ser
             65                  70                  75

Thr Ala Tyr Met Glu Leu Ser Ser Leu Arg Ser Glu Asp Thr Ala Val
         80                  85                  90

Tyr Tyr Cys Ala Arg Phe Ser His Phe Ser Gly Ser Asn Tyr Asp Tyr
 95                 100                 105

Phe Asp Tyr Trp Gly Gln Gly Thr Leu Val Thr Val Ser Ser
110                 115                 120
```

(2) INFORMATION FOR SEQ ID NO:19:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
TGAAGAAAGC TTGCCGCCAC CATGGAGACC CCCGCCCAGC TGCTGTTCCT GCTGCTGCTG      60

TGGCTGCCCG ACACCACCGG CGACATCCTG CTGACCCAGA GCCCC                    105
```

(2) INFORMATION FOR SEQ ID NO:20:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
GATGTTGGTG CCGATGCTCT GGCTGGCCCT GCAGCTCAGG GTGGCCCTCT CGCCGGGGCT      60

CAGGCTCAGG GTGCCGGGGC TCTGGGTCAG CAGGA                                95
```

(2) INFORMATION FOR SEQ ID NO:21:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
CAGAGCATCG GCACCAACAT CCACTGGTAC CAGCAGAAGC CCGGCCAGGC CCCCAGGCTG      60

CTGATCAAGT ACGCC                                                      75
```

(2) INFORMATION FOR SEQ ID NO:22:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
AGGGTGAAGT CGGTGCCGCT GCCGCTGCCG CTGAACCTGC TGGGGATGCC GCTGATGCTC      60

TCGCTGGCGT ACTTGATCAG CAGCCTG                                         87
```

(2) INFORMATION FOR SEQ ID NO:23:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
GCGGCACCGA CTTCACCCTG ACCATCAGCA GGCTGGAGCC CGAGGACTTC GCCATGTACT      60

ACTGCCAGCA GAGCGACAGC TGGC                                            84
```

(2) INFORMATION FOR SEQ ID NO:24:

(i) SEQUENCE CHARACTERISTICS:
        (A) LENGTH: 82 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:24:

TTTGGATCCT TCTAGAATAC TCACGTTTGA TCTCCACCTT GGTGCCCTGG CCGAAGGTGG      60

TGGGCCAGCT GTCGCTCTGC TG                                              82

(2) INFORMATION FOR SEQ ID NO:25:

(i) SEQUENCE CHARACTERISTICS:
          (A) LENGTH: 97 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:25:

TGAAGAAAGC TTGCCGCCAC CATGGACTGG ACCTGGAGGG TGTTCTGCCT GCTGGCCGTG      60

GCCCCCGGCG CCCACAGCCA GGTGCAGCTG GTGCAGA                              97

(2) INFORMATION FOR SEQ ID NO:26:

(i) SEQUENCE CHARACTERISTICS:
          (A) LENGTH: 103 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:26:

CAGCCAGTAC ATGCTGAAGG TGTAGCCGCT GGCCTTGCAG CTCACCTTCA CGCTGGCGCC      60

GGGCTTCTTC ACCTCGGCGC CGCTCTGCAC CAGCTGCACC TGG                       103

(2) INFORMATION FOR SEQ ID NO:27:

(i) SEQUENCE CHARACTERISTICS:
          (A) LENGTH: 105 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:27:

CACCTTCAGC ATGTACTGGC TGGAGTGGGT GAAGCAGAGG CCCGGCCACG GCCTGGAGTG      60

GGTGGGCGAG ATCAGCCCCG GCACCTTCAC CACCAACTAC AACGA                     105

(2) INFORMATION FOR SEQ ID NO:28:

(i) SEQUENCE CHARACTERISTICS:
          (A) LENGTH: 107 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:28:

GTCCTCGCTG GTCAGGCTGC TCAGCTCCAT GTAGGCGGTG TTGGTGCTGG TGTCGGCGGT      60

GAAGGTGGCC TTGGCCTTGA ACTTCTCGTT GTAGTTGGTG GTGAAGG                   107

-continued (2) INFORMATION FOR SEQ ID NO:29:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
AGCAGCCTGA CCAGCGAGGA CACCGCCGTG TACTACTGCG CCAGGTTCAG CCACTTCAGC      60

GGCAGCAACT ACGACTACTT CGA                                             83
```

(2) INFORMATION FOR SEQ ID NO:30:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
TTTGGATCCT TCTAGAACTC ACCTGAGCTC ACGGTCACCA GGGTGCCCTG GCCCCAGTAG      60

TCGAAGTAGT CGTAGTTGCT GCC                                             83
```

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

```
TGAAGAAAGC TTGCCGCCAC C                                               21
```

(2) INFORMATION FOR SEQ ID NO:32:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

```
TTTGGATCCT TCTAGAACTC ACC                                             23
```

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

```
TTTGGATCCT TCTAGAATAC TCAC                                            24
```

(2) INFORMATION FOR SEQ ID NO:34:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

AACAGCTATG ACCATG                                                     16

(2) INFORMATION FOR SEQ ID NO:35:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

CTGAACCTGT CGGGGATGCC GCTGATGCTC                                      30

(2) INFORMATION FOR SEQ ID NO:36:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

CCCGACAGGT TCAGCGGCAG CGGCA                                           25

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

GGTCAGCACG ATCTCGCCGG TG                                              22

(2) INFORMATION FOR SEQ ID NO:38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

GAGATCGTGC TGACCCAGAG CCCCGGC                                         27

(2) INFORMATION FOR SEQ ID NO:39:

(i) SEQUENCE CHARACTERISTICS:
        (A) LENGTH: 28 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

CCGGGGGCCT GCCTCACCCA CTCCAGCC                28

(2) INFORMATION FOR SEQ ID NO:40:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

GAGGCAGGCC CCCGGCCACG GCCTGGAGT                29

(2) INFORMATION FOR SEQ ID NO:41:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

GAAGGTGGCC CTGGCCTTGA ACTTCTCGTT GTAG                34

(2) INFORMATION FOR SEQ ID NO:42:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

CAAGGCCAGG GCCACCTTCA CCGCCGAC                28

(2) INFORMATION FOR SEQ ID NO:43:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

GTCCTCGCTC CTCAGGCTGC TCAGCTCCAT G                31

(2) INFORMATION FOR SEQ ID NO:44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

CAGCCTGAGG AGCGAGGACA C                                                       21

(2) INFORMATION FOR SEQ ID NO:45:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:45:

CCATCCACTC CAGCCTCTGG CCGGGCC                                                 27

(2) INFORMATION FOR SEQ ID NO:46:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:46:

CCATCCACTC CAGCCTCTGG CCGGGGGCCT GCC                                          33

(2) INFORMATION FOR SEQ ID NO:47:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:47:

CAGAGGCTGG AGTGGATGGG CGAGATC                                                 27

(2) INFORMATION FOR SEQ ID NO:48:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:48:

GTGCTGGCGC TGGTGTCGGC                                                         20

(2) INFORMATION FOR SEQ ID NO:49:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:49:

```
ACCAGCGCCA GCACCGCCTA C                                                    21
```

(2) INFORMATION FOR SEQ ID NO:50:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:50:

```
Met Tyr Trp Leu Glu
 1               5
```

(2) INFORMATION FOR SEQ ID NO:51:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:51:

```
Glu Ile Ser Pro Gly Thr Phe Thr Thr Asn Tyr Asn Glu Lys Phe Lys Ala
 1               5                  10                  15
```

(2) INFORMATION FOR SEQ ID NO:52:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:52:

```
Phe Ser His Phe Ser Gly Ser Asn Tyr Asp Tyr Phe Asp Tyr
 1               5                  10
```

(2) INFORMATION FOR SEQ ID NO:53:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:53:

```
Arg Ala Ser Gln Ser Ile Gly Thr Asn Ile His
 1               5                  11
```

(2) INFORMATION FOR SEQ ID NO:54:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:54:

```
Tyr Ala Ser Glu Ser Ile Ser
 1               5
```

(2) INFORMATION FOR SEQ ID NO:55:

```
    (i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:55:

Gln Gln Ser Asp Ser Trp Pro Thr Thr
1               5
```

RESHAPED MONOCLONAL ANTIBODIES AGAINST AN IMMUNOGLOBULIN ISOTYPE

This application is a continuation-in-part of abandoned U.S. application Ser. No. 07/952,802 filed Sep. 25, 1992. The invention relates to reshaped human monoclonal antibodies directed against isotypic determinants of immunoglobulin E (IgE), and derivatives of said antibodies. The antibodies and their derivatives are useful for in vitro and in vivo diagnostics, prophylaxis and treatment of allergy.

Allergy is a hypersensitive state induced by an exaggerated immune response to a foreign agent (the allergen). Immediate (type I) hypersensitivity, characterized by allergic reactions immediately following contact with the allergen, is mediated via B cells and is based on antigen-antibody reactions, whereas delayed hypersensitivity is mediated via T cells and based on mechanisms of cellular immunity. In recent years, the term "allergy" has become more and more synonymous with type I hypersensitivity.

Immediate hypersensitivity is based on the production of antibodies of the immunoglobulin class E (IgE antibodies) by B cells which upon confrontation with the allergen differentiate into antibody secreting plasma cells. The IgE induced reaction is a local event occurring at the site of the allergen's entry into the body, i.e. at mucosal surfaces and/or at local lymph nodes. Locally produced IgE will first sensitize local mast cells, i.e. IgE antibodies bind with their constant regions to $Fc_e$ receptors on the surface of the mast cells, and then "spill-over" IgE enters the circulation and binds to receptors on both circulating basophils and tissue-fixed mast cells throughout the body. When the bound IgE is subsequently contacted with the allergen, the $Fc_e$ receptors are crosslinked by binding of the allergen whereupon the cells degranulate and release a number of anaphylactic mediators such as histamine, prostaglandins, leukotrienes etc. It is the release of these substances which is responsible for the clinical symptoms typical of immediate hypersensitivity, namely contraction of smooth muscle in the respiratory tract or the intestine, the dilation of small blood vessels and the increase in their permeability to water and plasma proteins, the secretion of mucus resulting e.g. in rhinitis, atopic excema and asthma, and the stimulation of nerve endings in the skin resulting in itching and pain.

In addition, the reaction upon second contact with the allergen is intensified because some B cells form a "memory pool" of surface IgE positive B cells (sIgE$^+$ B cells) after the first contact with the allergen by expressing IgE on the cell surface.

A promising concept for the treatment of allergy involves the application of monoclonal antibodies, which are IgE isotype-specific and are thus capable of binding IgE. This approach is based on the inhibition of allergic reactions by downregulating the IgE immune response, which is the earliest event in the induction of allergy and provides for the maintenance of the allergic state. As the response of other antibody classes is not affected, both an immediate and a long lasting effect on allergic symptoms is achieved. In addition, antibodies suitable as anti-allergic agents should react with surface IgE positive B cells which into IgE producing plasma cells, so that they can be used to functionally eliminate those B cells. However, antibodies to IgE in principle may also induce mediator release from IgE sensitized mast cells by crosslinking the $Fc_e$ receptors, thus antagonizing the beneficial effect exerted on the serum IgE and sIgE$^+$ B cell level. In consequence, antibodies applicable in therapy of allergy must not be capable of reacting with IgE bound on sensitized mast cells and basophils, but should retain the capability to recognize sigE$^+$ B cells.

Such IgE isotype-specific antibodies have been described e.g. by Chang et al. (Biotechnology 8, 122–126 (1990)), in PCT application Ser. No. 89/06138 and European Patent Application No. 396505. However, as the disclosed antibodies are not of human origin they are less suitable for application to humans due to their immunogenicity as foreign proteins, their rather long persistence in the circulation, and the conceivable formation of damaging immune complexes. These drawbacks may potentially be reduced by transforming e.g. a rodent anti-IgE monoclonal antibody into a chimeric antibody which combines the variable domains of the rodent antibody with human antibody constant domains. This approach conserves the antigen-binding site of the rodent parent anti-IgE antibody, while conferring the human isotype and effector functions.

However, for use in humans such a chimeric antibody may not have sufficient clinical advantages over the original rodent antibody.

The immunogenicity of a chimeric antibody can be further reduced by grafting rodent hypervariable regions, also termed complementarity determining regions (CDRs), into the frameworks of human light and heavy chain variable region domains resulting in reshaped human antibodies. The technique involves the substitution or recombinant grafting of antigen-specific rodent CDR sequences for those existent within "generic" human heaviy and light chain variable domains (European Patent Application No. 239 400). It is reasoned that this technique will transfer the critical and major portion of the antigen-binding site to the human antibody.

Natural intact immunoglobulins or antibodies comprise a generally Y-shaped tetrameric molecule having an antigen binding-site at the end of each upper arm. An antigen binding site consists of the variable domain of a heavy chain associated with the variable domain of a light chain. More specifically, the antigen binding site of an antibody is essentially formed by the 3 CDRs of the variable domain of a heavy chain ($V_H$) and the 3 CDRs of the variable domain of the light chain ($V_L$). In both $V_L$ and $V_H$ the CDRs alternate with 4 framework regions (FRs) forming a polypeptide chain of the general formula $$FR1\text{-}CDR1\text{-}FR2\text{-}CDR2\text{-}FR3\text{-}CDR3\text{-}FR4 \qquad (I),$$

wherein the polypeptide chain is described as starting at the N-terminal extremity and ending at the C-terminal extremity. The CDRs of $V_H$ and $V_L$ are also referred to as H1, H2, H3, and L1, L2, L3, respectively. The determination as to what constitutes an FR or a CDR is usually made by comparing the amino acid sequences of a number of antibodies raised in the same species and general rules for identification are known in the art ("Sequences of proteins of immunological interest", Kabat E. A. et al., US department of health and human service, Public health service, National Institute of Health).

Recently it has been found that the contribution made by a light chain variable domain to the energetics of binding is small as compared with that made by the associated heavy chain variable domain, and that isolated heavy chain variable domains have an antigen binding activity on their own. Such molecules are commonly referred to as single domain antibodies (Ward, E. S. et al., Nature 341, 544–546 (1989)).

The CDRs form loops which, within the domains, are connected to a b-sheet framework. The relationship between amino acid sequence and structure of a loop can be described by a canonical structure model (Chothia et al., Nature 342, 887–883 (1989)). According to this model, antibodies have only a few main-chain conformations or 'canonical structures' for each hypervariable region. The conformations are determined by the presence of a few key amino acid residues at specific sites in the CDRs and, for certain loops, in the framework regions. Hypervariable regions that have the same conformations in different immunoglobulins have the same or very similar amino acid residues at these sites.

CDR grafting has been carried out for several rodent monoclonal antibodies yielding reshaped human (or humanized) antibodies with a binding affinity significantly lower than that of the rodent CDR-donor antibody. Recent findings have indicated that in addition to the transfer of CDRs changes within the framework of the human sequence may be necessary to provide satisfactory antigen binding activity in the CDR-grafted product.

Queen et al. (Proc. Natl. Acad. Sci. USA 86, 10029–10033 (1989)) have disclosed that the CDRs from a murine anti-Tac monoclonal antibody can be grafted into a human framework. The human frameworks were chosen to maximize homology with the murine sequence. The authors used a computer model of the murine parent antibody to identify amino acid residues located within the FRs that are close enough to interact with the CDRs or antigen. These residues were mutated to the residue found in the murine sequence. The humanized anti-Tac antibody had an affinity that was only about 1/3 that of the murine anti-Tac antibody and maintenance of the human character of this antibody was problematic.

Surprisingly, it has now been found that it is possible to produce reshaped human antibodies directed against human IgE, having an antigen, i.e. IgE, binding affinity which about equals or even exceeds that of the murine CDR-donor antibody.

Accordingly, it is one object of the present invention to provide a reshaped human monoclonal antibody specific for IgE comprising at least one antigen binding site comprising, in sequence, the hypervariable regions CDR1, CDR2 and CDR3; said CDR1 having the amino acid sequence Met-Tyr-Trp-Leu-Glu (SEQ ID NO. 50), said CDR2 having the amino acid sequence Glu-Ile-Ser-Pro-Gly-Thr-Phe-Thr-Thr-Asn-Tyr-Asn-Glu-Lys-Phe-Lys-Ala (SEQ ID NO. 51), said CDR3 having the sequence Phe-Ser-His-Phe-Ser-Gly-Ser-Asn-Tyr-Asp-Tyr-Phe-Asp-Tyr (SEQ ID NO. 52), said reshaped human antibody having an antigen binding affinity which at least about equals that of the murine CDR-donor antibody, a direct equivalent or a derivative of said reshaped antibody. In the amino acid sequence depicted in SEQ ID NO:1 CDR1 extends from amino acid 31 to 35, CDR2 extends from amino acid 50 to 66 and CDR3 extends from amino acid 99 to 112. The murine CDR-donor antibody is monoclonal antibody TES-C,21.

Preferably, the invention relates to a reshaped human antibody comprising at least one antigen binding site comprising:

a) a first domain comprising, in sequence, the hypervariable regions CDR1, CDR2 and CDR3, said CDR1 having the amino acid sequence Met-Tyr-Trp-Leu-Glu (SEQ ID NO. 50), said CDR2 having the amino acid sequence Glu-Ile-Ser-Pro-Gly-Thr-Phe-Thr-Thr-Asn-TyrAsn-Glu-Lys-Phe-Lys-Ala (SEQ ID NO. 51), said CDR3 having the amino acid sequence Phe-Ser-His-Phe-Ser-Gly-Ser-Asn-Tyr-Asp-Tyr-Phe-Asp-Tyr (SEQ ID NO. 52); and b) a second domain comprising, in sequence, the hypervariable regions CDR1, CDR2 and CDR3, said CDR1 having the amino acid sequence Arg-Ala-Ser-Gln-Ser-Ile-Gly-Thr-Asn-lle-His (SEQ ID NO. 53), said CDR2 having the amino acid sequence Tyr-Ala-Ser-Glu-Ser-lle-Ser (SEQ ID NO. 54), said CDR3 having the amino acid sequence Gln-Gln-Ser-Asp-Ser-Trp-Pro-Thr-Thr (SEQ ID NO. 55), said reshaped human antibody having an antigen binding affinity which at least about equals that of the murine CDR-donor antibody, a direct equivalent or a derivative of said reshaped antibody. CDR1, CDR2 and CDR3 of the first domain are the CDRs of the protein the sequence of which is identified in SEQ ID NO.1. CDR1, CDR2 and CDR3 of the second domain extend from amino acid 24 to 34, 50 to 56 and 89 to 87, respectively, in the amino acid sequence depicted in SEQ ID NO:3.

When the antigen binding site comprises both the first and second domains, these may be located on the same polypeptide chain or, preferably, each domain may be on a different chain, the first domain being part of an immunoglobulin heavy chain, or fragment therof, and the second domain being part of an immunoglobulin light chain or fragment thereof.

According to the invention a reshaped human antibody refers to a molecule characterized in that (1) it comprises at least one antigen binding site in which each existing chain comprises a human-like framework and (2) any constant region present is at least substantially homologous to, preferably identical with, a human immunoglobulin constant region. As used herein, a "human-like framework" is a framework consisting in sequence of framework regions FR1, FR2, FR3 and FR4, which comprises at least about 70 or more, preferably at least about 75 or more, amino acids identical with those in a framework of a particular human immunoglobulin sequence. Hence, all parts except possibly the CDRs of a reshaped human antibody are substantially homologous to corresponding parts of one or more native human immunoglobulin sequences. For example, a reshaped human antibody would not encompass a chimeric antibody comprising a murine variable region and a human constant region.

A human-like framework may be identical with a framework of a particular human immunoglobulin, or, preferably may differ from the particular human framework, i.e. a limited number of amino acid residues may be inserted, deleted or replaced by other amino acid residues. Such modificatons may be confined to a single FR, i.e. FR1, FR2, FR:3 or FR4, or involve two, three or all of the four FRs. For example, a hydrophobic amino acid within the human acceptor framework may be replaced with another amino acid, preferably also a hydrophobic amino acid, e.g. a homologous amino acid, replaced with two amino acids, or deleted. Likewise a hydrophilic amino acid within the human framework may be substituted by another amino acid, two amino acids or deleted, whereby replacing amino acids preferably maintain the hydrogen bond structure of the original framework. Such modifications may be performed on a 'trial and error' basis, i.e. the effect thereof is assessed by comparing the antigen-binding affinity of the created reshaped human antibody with that of murine CDR-donor antibody TES-C21. Assays suitable for determination of the antigen binding affinity are described below.

In particular, a limited number of amino acid residues, preferably 1 to 12 residues, within a chosen human acceptor framework may be replaced with amino acid residues, present at corresponding positions in a murine monoclonal antibody (human H murine exchange), particularly murine antibody TES-C21, and/or with amino acid residues present at corresponding positions in a different human antibody (human H human exchange). Preferably, the envisaged substitution of (an) amino acid(s) is based on prior identification of particular framework residues to be regarded as potentially crucial for antigen binding arid/or $V_L/V_H$ packing. Such crucial amino acids include framework residues which, because of their special nature and/or location:

are believed to be in contact with, or located near to, amino acids within the CDRs of the antibody;

could be involved in critical interactions with the antigen;

are believed to be involved in maintaining the overall integrity of the paired $V_H/V_L$ structure, directly or indirectly influencing interactions within or between the $V_H$ and $V_L$ domains.

Methods known to be suitable for identification of so-called crucial amino acids include molecular modeling. For example, molecular models of an antigen binding site may be created and displayed on a computer monitor by using computer programs which are generally available and well known to those skilled in the art.

In particular, design of a reshaped antibody of the invention may comprise the following steps:

a) Construction of a plausible molecular model for $V_L$ and $V_H$ of murine antibody TES-C21, e.g. based on the amino acid sequences depicted in SEQ ID NOs. 1 and 3 and the corresponding solved structures of a murine antibody determined to be highly homologous by sequence matching. The solved structures may originate from the same murine antibody or from two different murine antibodies.

b) Selection of suitable human acceptor frameworks from $V_H$ and $V_L$ of known human immunoglobulin sequences, e.g. sequences obtainable from a publicly available database, such as the KABAT database ("Sequences of proteins of immunological interest", Kabat E. A. et al., US department of health and human service, Public health service, National Institute of Health). Suitable human acceptor frameworks are e.g. frameworks from particular immunoglobulins that are highly homologous, preferably unusually homologous as compared with the remaining sequences in the database, to $V_H$ and $V_L$ domains of antibody TES-C21, or, most preferably consensus frameworks from many human antibodies which are highly homologous to $V_H$ and $V_L$ domains of antibody TES-C21. The heavy and light chain framework sequences chosen for grafting need not be derived from the same human antibody, but preferably are from different human antibodies.

c) Construction of a molecular model of $V_H$ and $V_L$ of a reshaped human antibody comprising the CDRs of murine TES-C21 and the FRs from the selected human acceptor framework according to formula I.

d) Comparison of the molecular models obtainable in steps a) and c).

In a reshaped human antibody of the invention, one, some or all of the identified crucial amino acid residues may be substituted with another amino acid residue, in particular with the residue present at that particular position in antibody TES-C21. Preferably, an "original" amino acid residue within the selected human framework is not replaced if it is part of a postulated canonical structure or important in determining the structure of a hypervariable loop. However, substitution of amino acid residues may not be restricted to crucial amino acids. Preferably, changes affecting non-crucial residues are human-human type changes.

In a reshaped human antibody of the invention the amino acid Cys may be in the oxidized state forming -S-S-bridges.

Examples of a reshaped human antibody provided by the present invention include a single domain antibody, a single chain antibody as well as an intact multi-chain, e.g. a tetrameric, antibody comprising full length heavy and light chains and any fragment thereof, e.g. $F_v$, $F(ab')_2$, Fab' and Fab fragments.

A single domain antibody comprises a single antigen binding site comprising a single domain.

A single chain antibody (also termed scFv) essentially consists of the variable domains of a heavy and a light chain. Preferably, these variable domains are covalently linked via a short peptide linker comprising from about 10 to 30, particularly about 15 amino acids selected from glycine and serine. A preferred peptide linker is the 15 amino acid polypeptide consisting of three repetitive units of Gly-Gly-Gly-Gly-Ser. A single chain antibody does not include a constant part of either heavy or light chain.

The reshaped human antibody of the invention is specific for IgE, i.e. it is directed against an isotypic determinant of human IgE. Accordingly, the antibody of the invention recognizes an antigenic determinant on the e heavy chain common to immunoglobulins of class IgE, i.e. it reacts with IgE molecules of different specificities but does not react with immurioglobulins of other isotypes or with immunoglobulin light chains.

A reshaped antibody of the invention is required to have an IgE-binding affinity which at least about equals that of murine antibody TES-C21. As used herein before or hereinafter, the term "at least about equals" means that the IgE-binding affinity of the reshaped human antibody (test antibody), on a statistical basis, is at least about 90%, preferably higher than 90%, particularly within about 100% and about 250%, of reference antibody TES-C21. A reshaped antibody is to be compared against the corresponding structure of TES-C21. For example, if the reshaped antibody is a single domain antibody its affinity should be related to single domain TES-C21. This murine single domain antibody can be easily prepared based on the information given in SEQ ID NOs. 1 and 3. In the description, no distinction is made between "affinity" or "avidity" of an antibody, but the term "affinity" is to refer to either affinity or avidity.

Determination of affinities of the reference and the reshaped test antibody is to be performed in the same fashion, i.e. under identical conditions in the same assay. The antibodies compared with each other should have about the same degree of purity. It is preferred to use highly purified antibodies.

The binding affinity of an antibody for IgE is determined using a suitable quantitative assay which can be easily established by a person with ordinary skill in the art based on known techniques and principles.

A suitable parameter to be determined is the equilibrium constant $K_{aff}$ (affinity constant). A variety of mathematical equations have been developed to facilitate experimental calculations of affinity constants for the antibody-antigen interaction. Suitable experimental methods for the measurement of $K_{aff}$ may e.g. rely on the measurement of the bound to free antigen ratio, e.g the competitive radioimmunoassay (RIA) or the competitive enzyme-linked imrriunoadsorbent assay (EIA), or on the measurement of the total antibody concentration, e.g. the non-competitive, solid phase EIA described by Beatty et al. (J. Immunol. Meth. 100, 173–179 (1987)).

Preferably, $K_{aff}$ is determined analyzing real-time biospecific interaction (Jönsson, U. et al., Biotechniques 11, 620–627 (1991) of the antibody with the IgE antigen on a BIA core™ system using CM5 surface chips (Pharmacia Biosensor, Uppsala, Sweden). The assay is essentially performed according to the manufacturer's instruction and involves determination of the kinetic constants $k_{ass}$ and $k_{diss}$. A suitable antigen is e.g. commercially available human IgE provided e.g. by Serotec (e.g. BP 094, Dottikon Switzerland) or a chimeric antibody having a human e constant region such as SE 44 (Sun et al., J. Cell. Biol. 109, 289a (1989)). In particular, this assay comprises an experimental cycle comprising:

1) Immobilization of a so-called catching antibody on the chip surface by chemical means, i.e. for measurements involving murine antibody TES-C21 an anti-mouse antibody, e.g. anti-mouse IgG, or for measurements involving a reshaped human antibody of the invention an anti-human antibody, e.g. anti-human IgG is employed.

2) Binding reference or test antibody to the immobilized catching antibody

3) Contacting the bound reference or test antibody with a fixed concentration of antigen.

Preferably several, e.g. four, experimental cycles are performed using a constant amount of bound antibody and varying the (known) concentration of IgE. After completion of each cycle the surface is regenerated, e.g. with an acid such as HCl.

Design of a reshaped antibody of the invention aims at constructing an antibody exhibiting a high association rate ($k_{ass}$), preferably $2.5 \times 10^5$ $M^{-1}s^{-1}$ or higher, combined with a low dissociation rate ($k_{diss}$), preferably $1.9 \times 10^{-5}s^{-1}$ or lower.

As used herein, a direct equivalent of a rehaped human antibody of the invention is a reshaped human antibody comprising, in sequence, CDR1, CDR2 and CDR3 as shown in SEQ ID NO. 1 and, optionally, CDR1, CDR2 and CDR3 as shown in SEQ ID NO. 3, wherein within one variable domain up to four amino acid residues within the CDRs, i.e. one two, three or four amino within the CDRs are replaced with another amino acid. Thus, by the terrr "direct equivalents thereof" is meant either a single domain reshaped human antibody (protein Y)

(1) in which the hypervariable regions CDR1, CDR2 and CDR3 taken as a whole are at least 90 % homologous to the CDRs as shown in SEQ ID NO. 1 and, (2) which has an affinity for IgE which at least about equals that of the reference protein of the invention having FRs identical to those of protein Y but having CDRs identical with those in SEQ ID NO.1; or a reshaped antibody having two domains per binding site (protein Y')

(1) in which the hypervariable regions CDR1$_H$, CDR2$_H$, CDR3$_H$ and CDR1$_L$, CDR2$_L$, CDR3$_L$ taken as a whole are at least 80%, preferably 90% homologous to the CDRs as shown in SEQ ID NOs. 1 and 3, and (2) which has an affinity for IgE which at least about equals that of the reference protein of the invention having FRs and constant parts identical to those of protein Y' but having hypervariable regions CDR1$_H$, CDR2$_H$, CDR3$_H$ and CDR1$_L$, CDR2$_L$, CDR3$_L$ identical with those in SEQ ID NOs.1 and 3.

The latter criterion can be tested by determining $K_{aff}$, e.g. according to the method described above.

Murine monoclonal antibody TES-C21 displays (among others) the following characteristics, which are also common to a reshaped human antibody of the present invention:

it inhibits the binding of IgE to cells bearing Fc$_e$ receptors I or II;

binds specifically to human-IgE secreting cells;

does not recognize and bind IgE bound on the surface of cells bearing Fc$_e$ receptors I or II, for example sensitized mast cells and basophils, does not trigger mediator (e.g. histamine) release.

inhibits IgE formation in the immune response.

These characteristic abilities can be determined by methods known in the art, e.g. those disclosed in European Application No. 396505 which is herein incorporated by reference.

A preferred reshaped antibody, or a derivative thereof of the invention comprises at least:

a) one immunoglobulin heavy chain or a fragment thereof which comprises a variable domain comprising in sequence the hypervariable regions CDR1$_H$, CDR2$_H$ and CDR3$_H$ and the constant part or fragment thereof of a human heavy chain, said CDR1$_H$ having the amino acid sequence Met-Tyr-Trp-Leu-Glu (SEQ ID NO. 50), said CDR2$_H$ having the amino acid sequence Glu-Ile-Ser-Pro-Gly-Thr-Phe-Thr-ThrAsn-Tyr-Asn-Glu-Lys-Phe-Lys-Ala (SEQ ID NO. 51), said CDR3$_H$ having the sequence Phe-Ser-His-Phe-Ser-Gly-Ser-Asn-Tyr-Asp-Tyr-Phe-Asp-Tyr (SEQ ID NO. 52); and b) and one immunoglobulin light chain, or a fragment thereof, comprising a light chain variable domain comprising in sequence the hypervariable regions CDR1$_L$, CDR2$_L$ and CDR3$_L$ and the constant part, or a fragment thereof, of a human light chain, said CDR1$_L$ having the amino acid sequence Arg-Ala-Ser-Gln-Ser-Ile-Gly-Thr-Asn-Ile-His (SEQ ID NO. 53), said CDR2$_L$ having the amino acid sequence Tyr-Ala-Ser-Glu-Ser-Ile-Ser (SEQ ID NO. 54), said CDR3$_L$ having the amino acid sequence Gln-Gln-Ser-Asp-Ser-Trp-Pro-Thr-Thr (SEQ ID NO. 55).

A fragment of an immunoglobulin heavy or light chain is a heavy or light chain which is not a full length chain and comprises a variable domain and optionally part of the constant part of the chain.

More preferred is a reshaped human antibody, or a derivative thereof, comprising at least a) one heavy chain comprising a variable domain having an amino acid sequence substantially identical with that shown in SEQ ID NO. 11 starting with the amino acid at position 1 and ending with the amino acid at position 123 and the constant part of a human heavy chair; and b) one light chain comprising a variable domain having an amino acid sequence substantially identical with that shown in SEQ ID NO. 5 starting with the amino acid at position 1 and ending with the amino acid at position 107 and the constant part of a human light chain;

Particularly preferred is a reshaped human antibody or a derivative thereof comprising at least:

a) one heavy chain comprising a variable domain having an amino acid sequence substantially identical with that shown in SEQ ID NO. 13 starting with the amino acid at position 1 and ending with the amino acid at position 123 and the constant part of a human heavy chain; and b) one light chain comprising a variable domain having an amino acid sequence substantially identical with that shown in SEQ ID NO. 5 starting with the amino acid at position 1 and ending with the amino acid at position 107 and the constant part of a human light chain;

The residue designations given in the present application correspond with the linear numbering of the amino acid residues.

The constant part of a human heavy chain can be selected from any of the isotypes alpha (a), delta (d), gamma(g) or mu(μ). Heavy chains of various subclasses such as the IgG subclasses 1–4 can be used. Preferred is the constant part of the human g1 chain. The different classes and subclasses of heavy chains are involved in different effector functions and thus, by choosing the type of the heavy chain constant region, reshaped human antibodies with the desired effector functions can be produced. The constant part of a light chain is a lambda(l), or preferably a kappa(k) chain.

Most preferred is reshaped human antibody designated H3L1 produced by the cell line EH31.8.

The invention also concerns a derivative of a reshaped human antibody of the invention. A derivative of a reshaped human antibody has the antigenic specificity of said antibody. According to the invention a derivative is meant to be any molecule obtainable by modification of an antibody of the invention, e.g. by adsorption or chemical modification. For example, depending on the intended use of the derivative, an antibody of the invention may be derivatized by covalent or non-covalent attachment of another proteinaceous or non-proteinaceous molecule. Covalent attachment resulting in antibody conjugates is achieved e.g. using coupling techniques known in the art. In such conjugates, the antibody is bound to the conjugation partner directly or by way of a spacer or linker group. Examples of derivatives are radioactively labelled reshaped human antibodies and conjugates of a reshaped human antibody of the invention, e.g. with an enzyme, a fluorescent or chemiluminescent marker, a suitable cytotoxic or cytostatic substance, a metal chelate, a protein that is not an enzyme such as avidin, or with a non-proteinaceous molecule such as biotin.

Enzymes used for antibody conjugates of the invention are, for example, horseradish peroxidase, alkaline phosphatase, b-D-galactosidase, glucose oxidase, glucoamylase, carbonic anhydrase, acetylcholinesterase, lysozyme, malate dehydrogenase or glucose-6-phosphate dehydrogenase.

Fluorescent markers include fluorescein, fluorochrome, rhodamine, and the like.

Chemiluminescence markers are e.g. acridinium esters of luminol.

Examples of metal chelates are ethylenediaminetetraacetic acid (EDTA), diethylenetriamine- pentaacetic acid (DPTA), 1,4,8,11 -tetraazatetradecane, 1,4,8,11 -tetraazatetradecane-1,4,8,11 -tetraacetic acid, 1-oxa-4,7,12,15-tetraazaheptadecane-4,7, 12,15-tetraacetic acid, or the like.

Radioactively labelled antibodies or fragments of the invention contain e.g. radioactive iodine ($^{123}$I, $^{125}$I, $^{131}$I), tritium ($^{3}$H), carbon ($^{14}$C), sulfur ($^{35}$S), yttrium ($^{90}$Y), technetium ($^{99m}$Tc), or the like.

The invention further concerns a method for the manufacture of anti-IgE reshaped human antibodies, direct equivalents and derivatives thereof according to the invention.

The reshaped human antibody, a direct equivalent or a derivative thereof according to the invention is prepared by a process that is known E se, characterized in that suitable host cells as defined further below producing a protein of the invention, are multiplied in vitro or in vivo and, if required, the desired protein is isolated and, optionally, converted into a derivative thereof. A protein of the invention can be prepared by a process comprising culturing any suitable transformable host under conditions which allow the expression of salid protein, isolating said protein and, optionally, converting the isolated protein into another protein of the invention, e.g. by proteolytic cleavage, or into a derivative of the invention, e.g. by attachment of another compound, e.g. a protein or a non-proteinaceous molecule, as mentioned above.

In a preferred embodiment of the invention, there is provided a process for producing a multi- chain anti-IgE reshaped human antibody which comprises (1) culturing a suitable host cell which has been transformed with first and second DNA constructs of the invention as defined below and (2) recovering an active anti-IgE reshaped human antibody from the culture. In this context an active antibody is an antibody specifically binding to IgE. A multi-chain antibody is an antibody comprising at least one antigen-binding site comprising a heavy and a light chain variable domain.

Alternatively, the heavy and light chain may be separately recovered and reconstituted into an active antibody after in vitro folding. Appropriate reconstitution methods are well known in the art. Therefore a process for producing a multi-chain antibody of the invention may also comprise:

(1) culturing a first host cell which is transformed with a first DNA construct of the invention and recovering said heavy chain or fragment thereof from the culture and (2) culturing a second host cell which is transformed with a second DNA construct of the invention and recovering said light chain or fragment thereof from the culture and (3) reconstituting in vitro an active anti-IgE reshaped antibody from the heavy chain or fragment thereof obtained in (1) and the light chain or fragment thereof obtained in (2).

In a similar manner, there is also provided a process for producing a single chain or a single domain reshaped human antibody of the invention which comprises (1) culturing a host cell which is transformed with a DNA construct respectively encoding a single chain or single domain reshaped human antibody of the invention and (2) recovering said polypeptide from the culture.

Fragments of the reshaped human antibodies, for example Fab, Fab' or F(ab')$_2$ fragments, can be prepared by recombinant DNA techniques as described above or from an intact multi-chain reshaped human antibody prepared as mentioned above by methods known per se, e.g. by digestion with enzymes such as papain or pepsin and/or cleavage of disulfide bonds by chemical reduction.

Suitable host cells include eukaryotic cells, e.g. animal cells, plant cells and fungi, and prokaryotic cells, such as gram-positive and gram-negative bacteria, e.g. *E. coli*. Preferred eukaryotic host cells are cells of mammalian origin and yeast cells.

As used hereinbefore or hereinafter, in vitro means ex vivo, thus including e.g. cell culture and tissue culture conditions.

For example, multiplication of mammalian cells in vitro is carried out in suitable culture media, which are the customary standard culture media, such as Dulbecco's Modified Eagle Medium (DMEM) or RPMI 1640 medium, optionally replenished by a mammalian serum, e.g. fetal calf serum, or trace elements and growth sustaining supplements, e.g feeder cells such as normal mouse peritoneal exudate cells, spleen cells, bone marrow macrophages, 2-aminoethanol, insulin, transferrin, low density lipoprotein, oleic acid, or the like.

In vitro production provides relatively pure antibody preparations and allows scale-up to give large amounts of the desired antibodies. Techniques for bacterial cell, yeast and mammalian cell cultivation are known in the art and include homogeneous suspension culture, e.g. in an airlift reactor or in a continuous stirrer reactor, or immobilized or entrapped cell culture, e.g. in hollow fibres, microcapsules, on agarose microbeads or ceramic cartridges.

Large quantities of the desired reshaped human antibodies of the invention can also be obtained by multiplying mammalian cells in vivo. For this purpose, hybridomra cells producing the desired antibodies are injected into histocompatible mammals to cause growth of antibody-producing tumours. Optionally, the animals are primed with a hydrocarbon, especially mineral oils such as pristane (tetramethyl pentadecane), prior to the injection. After one to three weeks, the antibodies are isolated from the body fluids of those mammals. For example, transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The cell culture supernatants are screened for the desired reshaped human antibodies, preferentially with an enzyme immunoassay, e.g. a sandwich assay or a dot-assay, or a radioimmunoassay using human IgE as antigen. For example, a sandwich enzyme immunoassay may be used to determine whether correctly assembled immurioglobulins are present in cell culture supernatants, whereby an antibody directed to the light chain human constant region k or I (as appropriate) and another antibody directed to the heavy chain human constant region e.g. g of the desired subclass are used, one of which is coated to a solid support and the other one conjugated to an enzyme allowing detection with a suitable enzyme substrate. Such an immunoassay is, for example, an enzyme-linked immunoaldsorbent assay (ELISA) wherein a suitable carrier, e.g. plastic microtitre plates are coated with immunoglobulin E and incubated with the culture supernatant to be tested. Bound monoclonal antibodies are detected by incubation with an enzyme-labelled antibody recognizing the anti-IgE antibodies in the supernatant and by subsequent addition of an appropriate enzyme substrate solution. The enzyme substrate reaction results, for example, in a color change which can be observed by eye or with optical measuring devices.

For isolation of the reshaped human antibodies, the immunoglobulins in the culture supernatants or in the ascitic fluid may be concentrated, e.g. by precipitation with ammonium sulphate, dialysis against hygroscopic material such as PEG, filtration through selective membranes, or the like. If necessary and/or desired, the antibodies are purified by the customary chromatography methods, for example gel filtration, ion-exchange chromatography, hydrophobic interaction chromatography or affinity chromatography, e.g. immunoaffinitychromatography. Preferably, the reshaped human antibodies are isolated from cell supernatants containing them by a procedure comprising a chromatographic purification step, e.g. affinity chromatography, for example with Protein A (if the antibody of the invention comprises an Fc part), ion-exchange chromatography, and/or gel filtration.

The reshaped human antibody derivatives of the invention are prepared by methods known per se, e.g. by adsorption of the reshaped human antibodies to another compound or by coupling providing chemically bound conjugates. Conjugates of antibodies of the invention with a protein, e.g. an enzyme are prepared e.g. by reacting an antibody prepared as described above with the protein in the presence of a coupling agent, e.g. glutaraldehyde, periodate, N,N'-o-phenylenedimaleimide, N-(m-maleimidobenzoyloxy)-succinimide, N-(3-[2'-pyridyidithio]-propionoxy) succinimide, N-ethyl-N'-(3-dimethylaminopropyl)-carbodiimide or the like. Conjugates with biotin are prepared e.g. by reacting antibodies with an activated ester of biotin such as the biotin N-hydroxysuccinimide ester. Conjugates with fluorescent or chemiluminescent markers are prepared in the presence of a coupling agent, e.g. those listed above, or by reaction with an isothiocyanate, preferably fluorescein-isothiocyanate.

Reshaped antibodies radioactively labelled with iodine ($^{123}$I, $^{125}$I, $^{131}$I) are obtained from the antibodies of the invention by iodination according to methods known per se, for example with radioactive sodium or potassium iodide and a chemical oxidizing agent, such as sodium hypochlorite, chloramine T or the like, or an enzymatic oxidizing agent, such as lactoperoxidase, or glucose oxidase and glucose. Antibodies or fragments according to the invention are coupled to yttrium (90Y) for example by diethylenetriaminepentaacetic acid (DPTA)-chelation. Technetium-99m labelled antibodies or fragments are prepared by ligand exchange processes, for example by reducing pertechnate ($TcO_4^-$) with stanrious ion solution, chelating the reduced technetium onto a Sephadex column and applying the antibodies to this column, or by direct labelling techniques, e.g. by incubating pertechnate, a reducing agent such as $SnCl_2$, a buffer solution such as sodium-potassium phthalate solution, and the antibodies of the invention.

Conjugates of antibodies of the invention to a protein may also be prepared directly by recombinant DNA techniques, e.g. those described below.

The process for producing a reshaped human antibody, a direct equivalent or a derivative according to the invention should yield the desired protein in an amount sufficient for affinity and specificity determinations.

The invention also concerns recombinant DNAs coding for the reshaped human antibodies of the invention and direct equivalents thereof. In a very general manner, there are provided DNA molecules encoding a single domain reshaped human antibody of the invention, a single chain reshaped human antibody of the invention, a heavy or light chain or fragments thereof of a reshaped human antibody of the invention. By definition such DNAs comprise coding single stranded DNAs, double stranded DNAs consisting of said coding DNAs and complementary DNAs thereto, or these complementary (single stranded) DNAs themselves. More specifically, the invention relates to first and second DNA constructs as described below.

The first DNA construct encodes a heavy chain or a fragment thereof and comprises a) a first part which encodes a variable domain comprising alternatively FRs and CDRs, said CDRs being in sequence $CDR1_H$, $CDR2_H$ and $CDR3_H$, the amino acid sequences of which in SEQ ID NO.1 extend from positions 31 to 35, 50 to 66 and 99 to 112, respectively; this first part starting with a codon encoding the first amino acid of the variable domain and ending with a codon encoding the last amino acid of the variable domain, and optionally, b) a second part encoding a human heavy chain constant part or fragment thereof which starts with a codon encoding the first amino acid of the constant part of the heavy chain and ends with a codon encoding the last amino acid of the constant part or fragment thereof, followed by a nonsense codon. Preferably, this first part encodes a variable domain having an amino acid sequence substantially identical to the amino acid sequence depicted in SEQ ID NO. 13 starting with the amino acid at position 1 and ending with the amino acid at position 123. More preferably, the first part has the nucleotide sequence as shown in SEQ ID NO. 13 starting with the nucleotide at position 79 and ending with the nucleotide at position 447. The second part may be a DNA fragment of genomic origin (comprising introns) or a cDNA fragment (without introns). If present, a second part encoding the constant part of the g1 chain is preferred.

The second DNA construct encodes a light chain or a fragment thereof and comprises
  a) a first part which encodes a variable domain comprising alternatively FRs and CDRs, said CDRs being in sequence CDR1$_L$, CDR2$_L$ and CDR3$_L$, the amino acid sequences of which in SEQ ID NO. 3 extend from positions 24 to 34, 50 to 56 and 89 to 97, respectively; this first part starting with a codon encoding the first amino acid of the variable domain and ending with a codon encoding the last amino acid of the variable domain, and optionally
  b) a second part encoding a human light chain constant part or fragment thereof which starts with a codon encoding the first amino acid of the constant part of the light chain and ends with a codon encoding the last amino acid of the constant part or fragment thereof, followed by a nonsense codon. Preferably, this first part encodes a variable domain having an amino acid sequence substantially identical to the amino acid sequence depicted in SEQ ID NO. 5 starting with the amino acid at position 1 and ending with the amino acid at position 107. More preferably, the first part has the nucleotide sequence as shown in SEQ ID NO. 5 starting with the nucleotide at position 82 and ending with the nucleotide at position 403. The second part may be a DNA fragment of genomic origin (comprising introns) or a cDNA fragment (without introns). If present, a second part encoding the constant part of the κ chain is preferred.

Preferred are first and second DNA constructs comprising both the first and the second part. In this case the first and second parts may be separated by intron sequences.

Advantageously, the first and second DNA construct comprise a third part which is located upstream of the first part and which encodes a leader peptide; this third part starts with the codon encoding the first amino acid and ends with a codon encoding the last amino acid of the leader peptide. A suitable leader peptide is a peptide required for secretion of the chains by the host organism in which they are expressed and which is subsequently removed by the host. Preferably, the third parts of the first and second DNA constructs encode a leader peptide of an immunoglobulin gene. Most preferably, the third part of the first DNA construct encodes a leader peptide having an amino acid substantially identical with the sequence shown in SEQ ID NO. 13, starting with the amino acid at position −19 and ending with the amino acid at position −1. Also most preferably, the third part of the second DNA construct encodes ;a leader peptide having an amino acid substantially identical with the sequence shown in SEQ ID No. 5, starting with the amino acid at position −20 and ending with the amino acid at position −1.

The invention also concerns a recombinant DNA coding for a direct equivalent of a reshaped human antibody of the invention and a recombinant DNA coding for a conjugate of an antibody of the invention to a protein.

The present state of the art is such that a person with ordinary skill in the art Nill be able to synthesize the DNA molecules of the invention given the written information provided herein, i.e. the amino acid sequences of the CDRs and the DNA sequences coding therefor (SEQ ID NOs. 1 and 3). A suitable method for obtaining a DNA construct encoding a variable domain of a reshaped human antibody of the invention comprises the synthesis of a number of oligonucleotides, their amplification by the PCR method, and their splicing to give the desired DNA sequence. An alternative method for constructing a variable domain gene comprises:

cloning a gene encoding a human monoclonal antibody of whatever specificity, determining the DNA segments encoding the FRs and CDRs, removing the DNA segments encoding the CDRs, so that the DNA segments encoding the FRs are fused together with suitable restriction sites at the junctions, preparing double stranded synthetic CDR cassettes according to the above identified sequences in SEQ ID Nos. 1 and 3, said cassettes having sticky ends, ligating the cassettes at the junctions of the FRs (European Patent Application No. 239400).

If desired, the DNA constructs of the invention may be mutated by a variety of well-known standard procedures, e.g. by inducing random mutations or by site-directed mutagenesis. In a DNA construct coding for a reshaped human antibody of the invention mutagenesis may not lead to an alteration of any amino acid located within a CDR. In a DNA construct coding for a direct equivalent of a reshaped antibody of the invention a replacement of a nucleotide with another nucleotide may alter the amino acid sequence in one or more CDRs.

A DNA coding for a direct equivalents of the reshaped antibodies of the invention may be prepared according to procedures known in the art e.g. by random or site-directed mutation of a DNA coding for a reshaped antibody of the invention. A mutation which is not a silent mutation but results in the replacement of at least one amino acid residue located within a CDR may yield a DNA coding for a direct equivalent of a reshaped antibody of the invention, if the protein thus produced meets the above-mentioned criterion.

As used in the following part of the specification, a reshaped human antibody of the invention is meant to include direct equivalents thereof.

Furthermore the invention concerns a recombinant DNA which is a hybrid vector comprising at least one of the above described DNA constructs, e.g. an insert coding for a light chain variable domain and/or a heavy chain variable domain, said vector being capable of replicating in a prokaryotic and/or eukaryotic host.

Preferred hybrid vectors of the invention comprise an insert coding for a light chain as described hereinbefore, and/or an insert coding for a heavy chain as described hereinbefore.

The hybrid vectors of the invention comprise an origin of replication or an autonomously replicating sequence, one or more dominant marker sequences and, optionally, expression control sequences, signal sequences and additional restriction sites.

Preferably, the hybrid vector of the invention comprises an above-described insert operably linked to an expression control sequence, in particular those described hereinafter.

Vectors typically perform two functions in collaboration with compatible host cells. One function is to facilitate the cloning of the nucleic acid that encodes the immunoglobulin chain, i.e. to produce usable quantities of the nucleic acid (cloning vectors). The other function is to provide for replication and expression of the gene constructs in a suitable host, either by maintenance as an extrachromosomal element or by integration into the host chromosome (expression vectors). A cloning vector comprises the gene constructs as described above, an origin of replication or an autonomously replicating sequence, selectable marker sequences and, optionally, signal sequences and additional restriction sites. An expression vector additionally comprises expression control sequences essential for the transcription and translation of the genes.

An origin of replication or an autonomously replicating sequence is provided either by construction of the vector to include an exogeneous origin such as derived from Simian virus 40 (SV 40) or another viral source, or by the host cell chromosomal mechanisms.

The markers allow for selection of host cells which contain the vector. Selection markers include genes which confer resistance to heavy metals such as copper or to antibiotics such as tetracycline, ampicillin, geneticin (G-418), neomycin, kanamycin or hygromycin, or genes which complement a genetic lesion of the host cell such as the absence of thymidinie kinase, hypoxanthine phosphoryl transferase, dihydrofolate reductase or the like.

Signal sequences may be, for example, presequences or secretory leaders coding for a leader peptide directing the secretion of the antibody, splice signals, or the like.

As expression control sequences, the vector DNA comprises a promoter, sequences necessary for the initiation and termination of transcription and for stabilizing the mRNA and, optionally, enhancers and further regulatory sequences. A wide variety of promoting sequences may be employed, depending on the nature of the host cell. Promoters that are strong and at the same time well regulated are the most useful. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of viral or eukaryotic cDNAs, e.g. from the expression host. Enhancers are transcription-stimulating DNA sequences of genomic or viral origin, e.g. derived from Simian virus, polyoma virus, bovine papilloma virus, Moloney sarcoma virus, or particularly from human cytomegalovirus.

The various DNA segments of the vector DNA are operationally linked, i.e. they are contiguous and placed into a functional relationship with each other.

Examples of vectors which are suitable for replication and expression in an *E. coli* strain are bacteriophages, for example derivaitves of λ bacteriophages, or plasmids. Suitable vectors comprise a complete replicon, a marker gene, recognition sequences for restriction endonucleases, so that the foreign DNA and, if appropriate, the expression control sequence can be inserted at these sites, and optionally signal sequences and enhancers. An expression vector according to the invention comprises an expression cassette comprising a suitable promoter and a DNA construct as defined above, which DNA is controlled by said promoter.

Microbial promoters are, for example, the strong leftward promoter $P_L$ of bacteriophage λ which is controlled by a temperature sensitive repressor. Also suitable are *E. coli* promoters such as the lac (lactose) promoter regulated by the lac repressor and induced by isopropyl-βD-thiogalactoside, the trp (tryptophan) promoter regulated by the trp repressor and induced e.g. by tryptophan starvation, and the tac (hybrid trp-lac promoter) regulated by the lac repressor.

Vectors which are suitable for replication and expression in yeast contain a yeast replication start and a selective genetic marker for yeast. One group of such vectors includes so-called ars sequences (autonomous replication sequences) as origin of replication. These vectors are retained extrachromosomally within the yeast cell after the transformation and are replicated autonomously. Furthermore, vectors which contain all or part of the $2\mu$ (2mikron) plasmid DNA from *Saccharomyces cerevisiae* can be used. Such vectors will get integrated by recombination into $2\mu$ plasmids already existing within the cell, or replicate autonomously. $2\mu$ sequences are particularly suitable when high transformation frequency and high copy numbers are to be achieved.

Expression control sequences which are suitable for expression in yeast are, for example, those of highly expressed yeast genes. Thus, the promoters for the TRP1 gene, the ADHI or ADHII gene, acid phosphatase (PHO3 or PHO5) gene, isocytochrome gene or a promoter involved with the glycolytic pathway, such as the promoter of the enolase, glyceraldehyde-3-phosphate kinase (PGK), hexokinase, pyruvate decarboxylase, phosphofruclokinase, glucose-6-phosphate isomerase, 3-phosphoglycerate mutase, pyruvate kinase, triosephosphate isomerase, phosphoglucose isomerase and glucokinase genes, can be used.

Promoters suitable for mammalian host cells are obtainable from a human irrimunoglobulin gene or from viruses such as Simian virus 40 (SV 40), Rous sarcoma virus (RSV), adenovirus 2, bovine papilloma virus (BPV), papovavirus BK mutant (BKV), or mouse or human cyto-megalovirus (CMV). Preferred is the human CMV promoter. Alternatively, the vectors may comprise promoters from mammalian expression products, such as actin, collagen, myosin etc., or the native promoter and control sequences which are normally associated with the immunoglobulin gene sequences.

The vectors may be suitable for both prokaryotic and eukaryotic hosts. Once a DNA molecule of the invention is prepared it may be conveniently transferred into a suitable expression vector. Expression vectors comprising a suitable promoter or genes encoding heavy or light chain constant parts are publicly available.

The gene constructs for the light chain and for the heavy chain are sequentially or simultaneously transferred into the host cells with the help of two vectors. Alternatively, both heavy and light chains are cloned into the same hybrid vector and incorporated in a one step-procedure as a single construct into the host cells. A third alternative utilises co-transfection of unlinked DNA fragments.

The recombinant DNAs coding for the desired reshaped human antibody can be prepared, for example, by culturing a transformed host cell. In particular, such DNAs can be prepared by a method comprising a) preparing DNA coding for the variable heavy and/or light chain variable domain of a reshaped human antibody specific for IgE b) preparing DNA coding for the heavy and/or light chain constant region of a human antibody, e.g. by isolating DNA from a genomic library and selecting the desired DNAs coding for said constant regions of antibodies using DNA probes;

c) incorporating the DNA of step a) or the DNA of steps a) and b) into appropriate hybrid vectors;

d) transferring the obtained hybrid vectors into a recipient host cell or retrieving the DNA coding for the desired genes and transferring the unlinked DNA into a suitable recipient host cell, e) selecting and culturing the transformed host cell, and optionally f) isolating the desired DNA.

Genomic human DNA according to step b) of the process described above is isolated from suitable human tissue, preferably from human placenta or human foetal liver cells, according to methods known in the art. A genomic DNA library is constructed therefrom by limited digestion with suitable restriction endonucleases following established procedures. The genomic DNA library is replicated, e.g. on nitrocellulose membranes, and screened with a DNA probe for the DNA sequences of interest. The desired DNA may be amplified using PCR technology.

The transfer of the recombinant DNAs, e.g. the transfer of hybrid vectors, and the selection of transformed cells is described below.

Moreover, the invention relates to a suitable host cell transformed with the recombinant DNAs described above, namely a host cell which is transformed with a DNA encoding the light chain and/or a DNA encoding the heavy chain of the desired reshaped human antibody of the invention. It is preferred that the host cell contains a large number of copies of the vectors per cell.

The host cells of the present invention have to be capable of culture in vitro. suitable host cells are of prokaryotic or eukaryotic origin and include bacterial cells, particularly *E. coli*, yeasts, e.g. Saccharomyces cerevisiae, or mammalian cells. To provide a suitable environment for the production of functional tetrameric antibodies, host cells of eukaryotic, particularly mammalian or yeast origin are preferred since the biosynthesis of functional tetrameric antibody molecules requires correct nascent polypeptide chain folding and assembly. Procaryotic hosts, especially *E.coli*, may be used for the production of antibody fragments of the invention, e.g. Fab- and Fv-fragments.

Examples of suitable hosts are microorganisms which are devoid of or poor in restriction or modification enzymes, such as bacteria, in particular strains of *Escherichia coli*, and yeasts, for example *Saccharomyces cerevisiae*.

Preferred host cells according to the invention are mammalian cells, e.g. COS-7 cells, Bowes melanoma cells, chinese hamster ovary (CHO) cells, embryonic lung cells L-132 and mammalian cells of lymphoid origin, such as lymphoma, myeloma, hybridomai, trioma or quadroma cells. Most preferred are mouse myeloma NSO cells.

These host cells are transfected with the light (L-) chain-gene construct alone, with the heavy (H-) chain- gene construct alone, or with both, either sequentially or simultaneously transferred with the help of two separate vectors or in a one-step procedure by using a double-construct (L-chain/H-chain) vector as indicated hereinbefore. In the alternative, unlinked gene constructs may be transfected into the host cells either sequentially or simultaneously.

Preferred are host cells transfected with both gene constructs secreting reshaped human antibodies as described hereinbefore, particularly cell line EH31.8. Further examples of host cells of the invention are cells transfected with similar recombinant plasmids which contain alternative orientations of the H- and L-chain gene constructs, incorporating additional DNA elements to facilitate high levels of expression of the antibodies of the invention.

The host cells of the invention are genetically stable, produce and preferably secrete reshaped human antibodies of the invention of constant specificity and can be activated from deep-frozen cultures by thawing and recloning.

The transformed host cells are cultured by methods known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/or carbonates of sodium, potassium, magnesium and calcium. The medium furthermore contains, for example, growth-promoting substances, such as trace elements, for example iron, zinc, manganese and the like.

The medium is preferably chosen as to exert a selection pressure and prevent the growth of cells which have not been transformed or have lost the hybrid vector. Thus, for example, an antibiotic is added to the medium if the hybrid vector contains an antibiotic resistance gene as marker. If, for instance, a host cell is used which is auxotrophic in an essential amino acid whereas the hybrid vector contains a gene coding for an enzyme which complements the host defect, a minimal medium deficient of said amino acid is used to culture the transformed cells.

Culturing is effected by processes which are known in the art. The culture conditions, such as temperature, pH value of the medium and fermentation time, are chosen so that a maximum titer of the polypeptide or derivative of the invention is obtained. Thus, an *E. coli* or yeast strain is preferably cultured under aerobic conditions by submerged culture with shaking or stirring at a temperature of about 20° C. to 40° C., preferably at about 30° C., and a pH value of 4 to 8, preferably of about pH 7, for about 4 to 30 hours, preferably until maximum yields of the polypeptide or derivative of the invention are reached.

When the cell density has reached a sufficient value, the culture is interrupted and the polypeptide or derivative can be isolated. If the hybrid vector contains a suitable secretion signal sequence, the polypeptide or derivative is secreted by the transformed cell directly into the culture medium. Otherwise, the cells have to be destroyed, for example by treatment with a detergent such as SDS, NP-40%, Triton% or deoxycholic acid, lysed with lysozyme or a similarly acting enzyme, or disrupted by an osmotic shock or ultrasound. Break-up of the cells will also be required if the signal sequence directs the secretion of the desired protein into the cell periplasm. If yeast is used as a host microorganism, the cell wall may be removed by enzymatic digestion with a glucosidase. Alternatively or additionally, mechanical forces, such as shearing forces (e.g. French press, Dyno mill and the like) or shaking with glass beads or aluminium oxide, or alternating freezing, for example in liquid nitrogen, and thawing, for example at 30° C. to 40° C., as well as ultra-sound can be used to break the cells.

The cell supernatant or the solution obtained after centrifugation of the mixture obtained after breaking the cells, which contains proteins, nucleic acids and other cell constituents, is enriched in proteins, including the polypeptides of the invention, in a manner which is known per se. Thus, for example, most of the non-protein constituents are removed by polyethyleneimine treatment and the proteins including the polypeptides and derivatives of the invention are isolated e.g. by the methods mentioned above.

The invention also relates to processes for the preparation of transformed host cells characterized in that suitable recipient host cells as described hereinbefore are transformed with one or two vectors according to the invention, and the transformed cells are selected.

Transformation of microorganisms is carried out as described in the literature, for example for *S. cerevisiae* (A. Hinnen et al., Proc. Natl. Acad. Sci. USA 75: 1929, 1978), and for *E. Coli* (M. Mandel et al., J. Mol. Biol. 53: 159,1970).

Accordingly, the transformation procedure of *E. coli* cells includes, for example, $Ca^{2+}$ pretreatment of the cells so as to allow DNA uptake, and incubation with the hybrid vector. The subsequent selection of the transformed cells can be achieved, for example, by transferring the cells to a selective growth medium which allows separation of the transformed cells from the parent cells dependent on the nature of the marker sequence of the vector DNA. Preferably, a growth medium is used which does not allow growth of cells which do not contain the vector. The transformation of yeast comprises, for example, steps of enzymatic removal of the yeast cell wall by means of glucosidases, treatment of the obtained spheroplasts with the vector in the presence of polyethylene glycol and $Ca^{2+}$ ions, and regeneration of the cell wall by embedding the spheroplasts into agar. Preferably, the regeneration agar is prepared in a way to allow regeneration and selection of the transformed cells as described above at the same time.

Transformation of cells of higher eukaryotic origin, such as mammalian cell lines is preferably achieved by transfection. Transfection is carried out by conventional techniques, such as calcium phosphate precipitation, microinjection into the cell nucleus, protoplaet fusion, electroporation, i.e. introduction of DNA by a short electrical pulse which transiently increases the permeability of the cell membrane, or the like. Transfection may be carried out in the presence of helper compounds, e.g. diethylaminoethyldextran, dimethyl sulfoxide, glycerol, polyethylene glycol or the like, or as co-precipitates of vector DNA and calcium phosphate.

After the transfection procedure, transfected cells are identified and selected with the help of a selection procedure matching the selection marker of the DNA used for transifection. Selection markers include genes which confer resistance to heavy metals such as copper or to antibiotics, e.g. G-418 (geneticin, a neomycin-derivative) or hygromycin, or genes which complement a genetic lesion of the host cell such as the absence of thymidine kinase, hypoxanthine phosphoribosyl transferase, dihydrofolate reductase, or the like!. For example, if the DNA used for transfection comprises a marker for geneticin resistance, transformed cells are identified and separated from untransformed cells by culture in the presence of the antibiotic geneticin.

A reshaped human antibody according to the invention or a derivative thereof is useful for the qualitative and quantitative determination of IgE, especially in body fluids, e.g. in serum, in vitro and in vivo.

For instance, the reshaped human antibody or a derivative thereof can be used in any of the known immunoassays which rely on the binding interaction between the antigenic determinants of IgE and the paratopes of said antibody. Examples of such assays are radioimmunoassays (RIA), enzyme, immunofluoresence, chemiluminescence, immunoprecipitation, latex agglutination, or hemagglutination immunoassays.

The reshaped human antibody according to the invention can be used as such or in the form of radioactively labelled derivative in a radioimmunoassay (RIA). Any of the known modifications of a RIA can be used, for example soluble phase (homogeneous) RIA, solid phase (heterogeneous) RIA, single RIA or double (sandwich) RIA with direct or indirect (competitive) determination of IgE.

An example of such a radioimmunoassay is a sandwich RIA in which a suitable carrier, for example the plastic surface of a microtitre plate or of a test tube, e.g. of polystyrene, polypropylene or polyvinylchloride, glass or plastic beads, filter paper, dextran etc., cellulose acetate or nitrocellulose sheets, magnetic particles or the like, is coated with an antibody of the invention by simple adsorption or optionally after activation of the carrier. Then test solutions containing IgE and finally a reshaped antibody which also reacts with the antigen and which is radioactively labelled, e.g. with $^{125}I$, is added. The amount of IgE in the test solutions is directly proportional to the amount of bound reshaped antibody and is determined by measuring the radioactivity bound to the carrier.

A reshaped human antibody according to the invention can be used as such or in the form of an enzyme-conjugated derivative in an enzyme immunoassay. As described above for radioimmunoassays, any of the known modifications of an enzyme immunoassay can be used.

The tests are carried out in an analogous manner to the radioimmunoassays described above using an enzyme label instead of a radioactive label. The amount of immune complex formed which corresponds to the amount of IgE present in the test solutions is determined by adding an enzyme substrate solution. The enzyme substrate reaction results, for example, in a color change which can be observed by eye or with optical measuring devices.

A reshaped antibody according to the invention can be used as such or in the form of a derivative conjugated with chemiluminescent markers in a chemiluminescence assay. As described above for radioimmunoassays, any of the known modifications of a chemiluminescence assay can be used.

The tests are carried out in an analogous manner to the radioimmunoassays described above using a chemiluminescent label instead of a radioactive label. The amount of immune complex formed which corresponds to the amount of IgE present in the test solutions is determined by adding a compound triggering luminescence, e.g. $H_2O_2$ and NaOH, and measuring the emission of light with optical measuring devices.

The use according to the invention of a reshaped human antibody or a derivative thereof as described hereinbefore for the determination of IgE also includes other immunoassays known per se, for example immunofluorescence assays, latex agglutination with antibody-coated or antigen-coated latex particles, hemagglutination with antibody-coated or antigen-coated red blood corpuscles, evanescent light assays using an antibody-coated optical fibre and other direct-acting immunosensors which convert the binding event into an electrical or optical signal, or the like.

A reshaped human antibody according to the invention or a derivative thereof is also useful for the determination of IgE-producing cells, preferentially in a plaque forming cell (PFC) assay.

A plaque forming cell assay according to the invention is based on the princip es of a solid phase immunoassay. Any of the known modifications of a solid phase immunoassay can be used, for example a radioimmunoassay, an enzyme, immunofluorescence or chemiluminescence immunoassay, or the like.

An example of such a plaque forming cell assay is a PFC assay based on an enzyme-linked immunosorbent assay (ELISA). For determination of the total amount of IgE-producing cells, a suitable carrier as described above for a sandwich RIA is coated with an antibody of the invention. A suspension of IgE-producing cells which are obtained from body fluids containing such cells by centrifugation, filtration, or the like, and a second polyclonal or monoclonal antibody specific for IgE, e.g. an antibody of the invention recognizing a different epitope of IgE than the first antibody, which is conjugated with an enzyme, e.g. alkaline phosphatase, are added. The amount of IgE-producing cells in the test suspensions is directly proportional to the amount of bound second antibody and is determined by adding an appropriate substrate solution, which results for example in the development of a colored reaction product, and counting the colored spots (plaques). For determination of the fraction of IgE-producing cells which produce IgE directed against a specific allergen, the carrier is first coated with the allergen or an adsorbable conjugate of the allergen before adding a cell suspension as described above. The fraction of IgE in the test suspension which is directed against the allergen binds to the surface-bound allergen and is determined by adding an antibody of the invention conjugated with an enzyme and an appropriate substrate solution resulting for example in the development of a coloured reaction product, and counting the colored spots (plaques).

Furthermore, the invention concerns test kits for the qualitative and quantitative determination of IgE and/or IgE producing cells comprising monoclonal antibodies and/or derivatives thereof of the invention and, optionally, other monoclonal or polyclonal antibodies anchor adjuncts.

Test kits according to the invention for a radioimmunoassay contain, for example, a suitable carrier, optionally freeze-dried or concentrated solutions of one or more monoclonal antibodies, solutions of a radioactively labelled monoclonal antibody or of radioactively labelled IgE, standard solutions of IgE, buffer solutions and, optionally, detergents for preventing non-specific adsorption and aggregate formation, pipettes, reaction vessels, calibration curves and the like. One or more of the monoclonal antibodies of the test kit are monoclonal antibodies of the invention. Test kits for the determination of IgE-producing cells which produce IgE directed against a specific allergen additionally contain solutions of the allergen or an adsorbable conjugate of the allergen.

Test kits according to the invention for an enzyme-immunoassay contain, for example, a suitable carrier, optionally freeze-dried or concentrated solutions of one or more monoclonal antibodies, optionally freeze-dried or concentrated solutions of an enzyme-labelled monoclonal antibody, of enzyme-labelled IgE, of a polyclonal anti-IgE serum and/or of enzyme-labelled monoclonal or polyclonal antibodies that recognize and bind the anti-IgE antibody, enzyme substrates in solid or dissolved form, standard solutions of IgE, buffer solutions, detergents, pipettes, reaction vessels, calibration curves, color scale tables and the like. One or more of the monoclonal antibodies of the test kit are monoclonal antibodies of the invention. Test kits for the determination of IgE-producing cells which produce IgE directed against a specific allergen additionally contain solutions of the allergen or an adsorbable conjugate of the allergen.

Moreover, the reshaped human antibodies according to the invention and their derivatives can be used for the qualitative and quantitative determination of surface IgE positive (sIgE$^+$) B cells by any of the known conventional staining techniques, e.g. by flow cytometric analysis.

In addition, the monoclonal antibodies of the invention and/or their derivatives are useful for the treatment and/or prophylaxis of allergy.

The therapeutic effect is achieved by downregulating the IgE immune response due to the specific characteristics of the reshaped human antibodies and derivatives thereof according to the invention:

They are capable of neutralizing formed IgE by binding free IgE and inhibiting the binding of IgE to cells bearing Fc$_e$ receptors I or II, in particular mast cells and basophils.

They recognize and bind IgE expressed on the surface of surface IgE positive B cells (sIgE$^+$ B cells) and are therefore useful in depleting the population of such cells which form a "memory pool" resulting in IgE production after a second exposure to the allergen. The possibility of producing reshaped human antibodies of chosen immunoglobulin (sub)classes allows the activation of cellular mechanisms of the host immune system resulting in specific killing of the sIgE$^+$ B cells. This can also be achieved by conjugates of the monoclonal antibodies of the invention with cytotoxic drugs which will deliver such drugs to the target cells.

Since the reshaped human antibodies of the invention and their derivatives do not recognize cytophilic IgE on cells bearing Fc$_e$ receptors I or II, e.g. mast cells and basophils, they do not induce mediator release by these cells.

The monoclonal antibodies and derivatives thereof according to the invention also have a long lasting therapeutic effect because they have a significant inhibitory effect on the formation of IgE in the immune response.

In consequence, the reshaped human antibodies of the invention and their derivatives provide a treatment that, rather than treating symptoms, actually affects the underlying cause of allergy, for example by removal of IgE antibodies and surface IgE positive B cells, thus eliminating the potential for an allergic response, and inhibition of IgE formation. It is especially advantageous that the treatment does not require ongoing repeated doses, and that the reshaped human antibodies and their derivatives of the invention can be used for prophylactic treatment by administration prior to detection of any of the symptoms of allergy.

As they are only weakly immunogenic or non-immunogenic when administered to humans the reshaped human antibodies and derivatives thereof according to the invention are especially useful for in vivo diagnostics, therapeutic applications and prophylaxis. Preferably, the reshaped human antibodies are tolerated by the human organism as self proteins when administered for therapeutic purposes.

The therapeutic daily dose for mammals is between approximately 0.1 mg and 10 mg per kg body weight depending on the status of the patient and the mode of application.

The invention also relates to pharmaceutical preparations comprising a reshaped human antibody and/or derivatives thereof according to the invention. The pharmaceutical preparations comprise, for example, the reshaped human antibodies and/or derivatives thereof in a therapeutically effective amount together or in admixture with inorganic or organic, solid or liquid pharmaceutical carriers.

Preferred are pharmaceutical preparations for parenteral application and inhalation. Preparations for intramuscular, subcutaneous or intravenous application or for inhalation are e.g. isotonic aqueous solutions or suspensions, optionally prepared shortly before use from lyophilized or concentrated preparations. The pharmaceutical preparations may be sterilized and contain adjuvants e.g. for conserving, stabilizing, wetting, emulsifying or solubilizing the ingredients, salts for the regulation of the osmotic pressure, buffer and/or compounds regulating the viscosity, e.g. sodium carboxycellulose, dextran, polyvinylpyrrolidone or gelatine. They are prepared by methods known in the art, e.g. by conventional mixing, dissolving or lyophilizing, and contain from approximately 0.01% to approximately 50% of active ingredients. The preparations for injections are processed, filled into ampoules, vials or disposable injection devices, and sealed under aseptic conditions according to methods known in the art.

The pharmaceutical preparations of the invention may be used for the prophylaxis and treatment of allergic reactions in humans, in particular those typical of immediate type hypersensitivity as associated e.g. with allergic asthma, allergic rhinitis and atopic excema.

Figure 1:
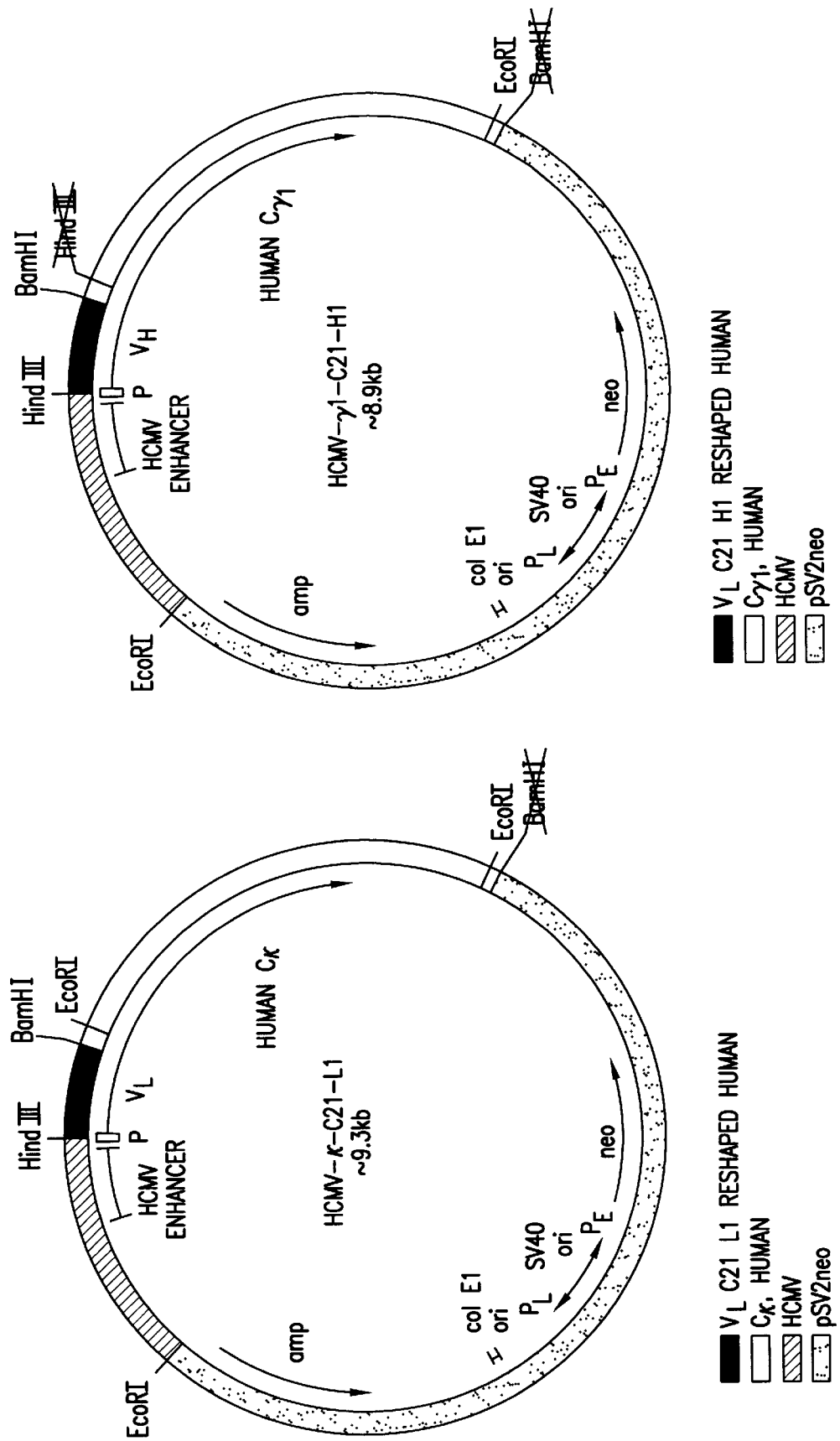
FIG. 1: HCMV- mammalian expression vectors used to produce C21-L1 fused to the human κ light chain constant domain and C21-H1 fused to the human γ1 heavy chain constant domain.

The invention particularly concerns the reshaped human antibodies, the recombinant DNAs, the transformed host cells, and the method for the preparation thereof as described in the Examples. The following examples illustrate the invention but do not limit it to any extent.

Abbreviations: $V_L$=light chain variable region; $V_H$=heavy chain variable region; CDR=complementarity determining region; FR=framework region; HCMV=Human Cytomegalovirus Materials Human IgGs with κ light chains, purified from human plasma, are all purchased from Sigma, Buchs, Switzerland (IgG1: I-3889, IgG2: I-4139, IgG3: I-4389 and IgG4: I-4639). Human IgM (Cat.No. PHP003) and human IgD (Cat.No. PHP005) from human myeloma serum are obtained from Serotec. IgAs from human plasma (IgA1: 400105; IgA2: 400108) are from Calbiochem, Läufelfingen, Switzerland.

EXAMPLE 1

Molecular Modelling of mAb C21 $V_L$ and $V_H$

A molecular model of the $V_L$ (SEQ. ID. NO. 2) and $V_H$ (SEQ. ID NO. 4) regions of mouse monoclonal antibody C21, which recognizes human IgE, is built, for $V_L$, on the solved structure of the highly homologous mouse anti-lysozyme antibody HyHEL-10 (Padlan, E. A., Silverton, E. W., Sheriff, S., Cohen, G. H., Smith-Gill and Davies, D. R., 1989, Proc. Nati. Acad. Sci., USA, 86:5938; referred to as sequence 3 HFM in the Brookhaven Database, Bernsiein et al., J. Mol. Biol 112, 535–542 (1977)) and, for $V_H$, on the structure of the mouse anti-lysozyme antibody HyHEL-5 (Sheriff, S., Silverton, E. W., Padlan, E. A., Cohen, G. H., Smith-Gill, S. J., Binzel, B. C. and Davies, D. R., 1987, Proc. Natl. Acad. Sci., USA, 84:8075; referred to as sequence 2 HFL in the Brookhaven Database, supra). The light and heavy chain variable regions of mAb C21 and HyHEL-10 or HyHEL-5 have 91% and 90% amino acid identity, respectively. The model is built on a Silicon Graphics IRIS 4D workstation running under the UNIX operating system and using the molecular modelling package QUANTA (Polygen Corp., USA). Identical residues in the framework are retained; non-identical residues are substituted using the maximal overlap procedure (Snow, M. E. and Amzel, L. M., 1986, Proteins 1:267) incorporated into QUANTA's protein modelling facility.

The complementarity determining regions CDR1 ($L_1$), CDR2 (L2) and CDR3 (L3) of the $V_L$ region and CDR1 ($H_1$) and CDR2 (H2) of the $V_H$ region from mouse C21 antibody correspond to canonical forms postulated previously (Chothia, C., Lesk, A. M., Tramontaro, A., Levitt, M., Smith-Gill, S. J., Air, G., Sherrif, S., Padlan, E. A., Davies, D., Tulip, W. R., Colman, P. M., Spinelli, S., Alzari, P. M. and Poljak, R. J., 1989, Nature, 342:877). The main chain torsion angles of these loops are kept as in the original antibody structures (HyHEL-10 for L1-L3 and HyHEL-5 for H1-H2). There are no canonical structures for the CDR3 (H3) of the $V_H$ regions, it is therefore modelled differently. Thirty candidate loops are extracted from 91 high resolution protein structures using a published algorithm (Jones, T. A. and Thirup, S., 1989, EMBO J., 5:819–822) as implemented in QUANTA, and the best version selected by eye. The loops are anchored on three framework residues on either side of the H3 CDR. Thus, H3 of the $V_H$ region is modelled on Bence-Jones protein RHE (Furey, W., Wang, B. C., Yoo, C. S. and San, M., 1983, J. Mol. Biol., 167:661–692) in the region of residues 87–106, which corresponds roughly to CDR3 (L3).

The model is subjected to steepest descents and conjugate gradients energy minimization using the CHARM potential (Brooks, B. R., Bruccoleri, R. E., Olafson, B. D., States, D. J., Swaminathan, S. and Karplus, M., 1983, J. Comp. Chem,. 4:187) as implemented in QUANTA in order to relieve unfavourable atomic contacts and to optimize Van der Waals and electrostatic interactions.

EXAMPLE 2

Design of Reshaped Human C21 $V_L$ and $V_H$ Regions

The design of reshaped human C21 $V_L$ and $V_H$ regions is based primarily on the consensus sequences of human $V_L$ and $V_H$ regions (versions C21-L1, C21-L2, C21-L3, C21-H1 and C21-H3) as found in the KABAT database (Kabat, E. A., Wu, T. T., Reid-Miller, M., Perry, H. M. and Gottesman, K. S., 1987, Sequences of Proteins of Immunological Interest, 4th Edition, U.S. Department of Health and Human Services, U.S. Government Printing Office). In addition, two more reshaped human C21 $V_H$ regions (C21-Hay1 and C21-Hay3) are based on the framework regions (FRs) of an individual human antibody.

For the design of consensus-based reshaped human C21 variable regions, the amino acid sequences of the $V_L$ and $V_H$ regions from mouse C21 antibody are compared with the consensus sequences for $V_L$ and $V_H$ regions of human antibodies from the KABAT database. This analysis reveals that the mouse C21 $V_L$ region and the mouse C21 $V_H$ region are most similar to the human κ $V_L$ subgroup III consensus sequence (77% amino acid sequence identity) and the human $V_H$ subgroup I consensus sequence (71% amino acid sequence identity), respectively. These human consensus sequences are used to design the reshaped human C21 light and heavy chain variable regions C21-L0 and C21-H0 containing murine C21 CDRs and the human FRs of the respective consensus sequence. The molecular models of the mouse C21 variable regions (Example 1) are used to identify framework residues that are potentially important to achieve good antigen binding and which might be critical for $V_L V_H$ packing. As a result of this graphical analysis, some of the noted human consensus amino acids within the FRs are exchanged for their corresponding mouse C21 residues. These changes are only considered within the human framework region if they do not fall into one of the following categories:

[1] The human consensus sequence (human subgroup 1; HSG1) reveals no dominant amino acid preference at this position, but the amino acid as found in the original mouse C21 sequence is present in at least one individual sequence of the respective human immunoglobulin variable region subgroup. For example, HSG 1 is described as having no consensus sequence at amino acid residue 19 (Kabat et al., supra) although several human antibodies have a Lys residue at this position. Since Lys also appears in the C21 sequence it is retained in the reshaped monoclonal antibody.

[2] The amino acid at the framework position is part of a postulated canonical structure, important in determining the structure of the CDRs or hypervariable loops, and is thus expected to be indispensible for maintaining the shape and integrity of the antigen binding site (Chothia, C. and Lesk, A. M., 1987, J. Mol. Biol., 196:901; Chothia, C. et al., 1989, supra).

According to these rules, four and six amino acids within the reshaped human light and heavy chain variable regions C21-L0 and C21-H0 are exchanged when compared with the human consensus sequences, resulting in versions C21-L1' and C21-H1. The positions of the exchanged amino acids are 1, 3, 49 and 60 in C21-L1' and its below-identified modified version C21-L1 (SEQ ID NO. 5). In C21-H1 (SEQ. ID NO. 11) the positions of the exchanged amino acids are 38, 40, 67, 68, 70 and 87. An exception to the above-mentioned rules is position 76 of the reshaped human C21 $V_H$ region, where we choose the most frequent human amino acid for this position (Thr) as found in the human $V_H$ consensus sequence.

Further new versions of $V_L$ and $V_H$ contain the following alterations (compared with C21-L1 and C21-H1, respectively):

C21-L2 (SEQ ID NO. 7): aspartic acid (instead of serine) at position 60;

C21-L3 (SEQ ID NO. 9): glutamic acid (instead of aspartic acid) at position 1; valine (instead of leucine) at position 3;

C21-H3 (SEQ ID NO. 13): arginine (instead of lysine) at position 38; alanine (instead of arginine) at position 40; arginine (instead of lysine) at position 67; arginine (instead of threonine) at position 87.

A database search using C21-L1' and C21-H1 reveals that reshaped human C21 $V_L$ version C21-L1' is most similar (91% sequence identity) to human κ light chain variabile region HUMIG KAF (EMBL database, Heidelberg, Germany; Newkirk, M. M., Gram, H., Heinrich, G. F., Oestberg, L., Capra, J. D. and Isserman, R. L., 1988, J. Clin. Invest., 81:1511–1518) and that reshaped human C21 $V_H$ version C21-H1 is most similar (78% sequence identity) to human heavy chain variable region HUMIG HAY (EMBL database, supra; Dersimonian, H., Schwartz, R. S., Barrett, K. J. and Stollar, B. D., 1987, J. Immunol., 139:2496–2501). These sequences are referred to below as KAF and HAY, respectively. The FRs of KAF and the human κ $V_L$ subgroup III consensus sequence differ only at positions 49 and 85. At position 49 the corresponding mouse C21 amino acid (lysine) is, retained, due to its putative antigen binding, whereas at position 85 the human $V_L$ III consensus amino acid valine is changed to methionine, as found in KAF. Thus, the modified version of C21-L1', designated C21-L1 (SEQ. ID. NO. 5), is based on the individual human light chain variable region KAF (Newkirk, M. M. et al., 1988, supra). It differs from the first version C21-L1' in that there is a methionine instead of a valine at position 85. The reshaped versions C21-L2 (SEQ ID NO. 7) and C21-L3 (SEQ ID NO. 9) also have a methionine at position 85.

In contrast, the FRs of human heavy chain variable region HAY and the human $V_H$ subgroup I consensus sequence differ at several positions. In order to construct reshaped human C21 $V_H$ regions that show a high degree of similarity to this individual human antibody, two more versions of reshaped human C21 $V_H$ regions are designed based on the FRs from the heavy chain variable region of human heavy chain variable region HAY. The construction of the HAY-based reshaped human C21 $V_H$ versions necessitate five changes in FR2 and FR3 of reshaped human C21 versions C21-H1 and C21-H3 at positions 43, 44, 48, 76 and 77, respectively. These HAY-based versions are called C21-Hay1 (SEQ ID NO. 15) and C21-Hay3 (SEQ. ID NO. 17), respectively. Two additional differences between the FRs of HAY and the human $V_H$ subgroup I consensus sequence at positions 30 and 72 are retained as in the mouse C21 $V_H$ region, and are not regarded as changes, because they are canonical residues that define the structure of the CDRs (Chothia, C. et al., 1989, supra).

EXAMPLE 3

Design and Construction of Humanized Antibody Genes

For the design of humanized antibody gene cassettes, additional sequences necessary for efficient expression and cloning are added at the 5'- and 3'-ends of the resulting coding regions. Eukaryotic leader sequences for efficient expression of reshaped human C21 antibodies are added in frame to the designed humanized variable regions. The leader sequence for the reshaped human C21 $V_L$ region is derived from the leader sequence found in the κ light chain of human antibody KAF (Newkirk, M. M. et al., 1988, supra) from which the variable region is used for reshaping of the C21 $V_L$ region. The leader sequence for the reshaped human C21 $V_H$ region is derived from the leader sequence found in the heavy chain of human antibody HG3 CL (Rechavi, G., Ram, D., Glazer, L., Zakut, R. and Givol, D., 1983, Proc. Natl. Acad. Sci., USA, 80:855–859), a member of human $V_H$ subgroup I (Kabat, E. A., Wu, T. T., Reid-Miller, M., Perry, H. M. and Gottesman, K. S., 1987, Sequences of Proteins of Immunoloclical Interest, 4th Edition, U.S. Department of Health and Human Services, U.S. Government Printing Office). The resulting protein sequences for reshaped human C21 $V_L/V_H$ regions are then back-translated into DNA sequences using the Codon Usage Table for mouse sequences, as found in the Sequence Analysis Software Package of the Genetics Computer Group, University of Wisconsin, USA. To the designed DNA fragments are also added eukaryotic translation signals at the 5-end (Kozak, M., 1987, J. Mol. Biol., 196: 947–950), donor splice sites at the 3'-end (Breathnach, R., Benoist, C., O'Hare, K., Gannon, F. and Chambon, P., 1978, Proc. Natl. Acad. Sci,. USA, 75:48534857) and Hind III (5'-ends) and Bam HI and Xba I (3'-ends) DNA restriction sites for convenient subdoning into the designated mammalian expression vectors.

The designed humanized antibody gene cassettes, encoding the reshaped human C21 $V_L$ and $V_H$ regions C21-L1 and C21-H1 are then constructed by gene synthesis using synthetic DNA polynucleotides. The entire DNA fragments are subdivided into six regions overlapping with each other by 20 nucleotides. For each reshaped human C21 variable region gene cassette, six 5'-phosphorylated and PAGE-purified polynucleotides designated C21-LA (SE:Q ID NO: 19), C21-LB (SEQ ID NO: 20), C21-LC (SEQ ID NO: 21), C21-LD (SEQ ID NO: 27?), C21-LE (SEQ ID NO: 23), C21-LF (SEQ. ID NO: 24), C21-HA (SEQ ID NO: 25), C21-HB (SEQ ID NO: 26), C21-HC (SEQ ID NO: 27), C21-HD (SEQ ID NO: 28), C21-HE (SEQ ID NO: 29) to HF (SEQ. ID NOs. 30) are purchased from Genosys Biotechnologies, Houston, Tx., USA. They are then assembled in a polymerase chain reaction (PCR)-based gene synthesis. 5 pmol of each polynucleotide (i.e. LA to LF) are first annealed and extended in a 100 μl reaction containing 1 0 mM Tris-HCl pH 8.3, 1.5 mM $MgCl_2$, 50 mM KCl, 10 mM β-mercaptoethanol, 0.05% (w/v) Tween-20, 0.05% NP-40 (Merck, Zürich), 200 μM dNTPs (N=G, A, T or C) and 5 U VentTM DNA polymerase (New England Biolabs).

Temperature steps are 95° C./1 min, 50° C./2 min and 72° C./4 min using a Techne PHC-2 temperature cycler. After this first cycle, 50 pmol of oligonucleotide primers C21–5' (SEQ ID NO. 31) and C21-L3' (SEQ ID NO. 33) or C21-H3' (SEQ ID NO. 32) hybridizing at the 5'- and 3'-ends of the desired, full-length DNA fragment are added and the full-length DNA fragment amplified in a PCR reaction of about :20 cycles using the following cycling parameters: 95° C./1 min, 60° C./2 min and 72° C./2 min. The PC then extracted once with one volume of chloroform and the DNA precipitated by adding 1/10 vol of 8 M LiCl and 3 vol of ethanol. The precipitated DNA is redissolved in $H_2O$ and digested with Hind III and Bam HI restriction endonucleases under conditions suggested by the supplier (Boehringer, Mannheim, Germany). DNA fragments of the expected sizes (C2 1-Li =416 bp and C21H1=459 bp) are electrophoretically purified in 1% agarose/TBE and excised from the gel. Gel pieces are cut into smaller fragments, frozen in liquid nitrogen for 5 min, and then eluted through glasswool by centrifugation in a microcentrifuge (30 min, 136000×g). After phenol-chloroform extraction and LiCl/ethanol precipitation at room temperature, the purified Hind III-Bam HI restriction fragments are subcloned into pBluescript KS II M13 +(Stratagene) and transfected into competent *E. coli* cells (HB101 strain from GIBCO-BRL). Multiple plasmid clones of either KS+C21/L1 or KS+C21/H1 containing DNA inserts of correct size are sequenced using Sequenase (USB). Point mutations and/or deletions within the DNA sequence are corrected by exchanging DNA restriction enzyme fragments belween different clones and/or oligonucleotide directed PCR mutagenesis according to a published procedure (Kammann, M., Laufs, J., Schell J. and Gronenborn B., 1989, Nucl. Acids Res., 17:5404). Hind III-Bam HI fragments exhibiting correct DNA sequences are then subcloned into the light or heavy chain expression vectors to create the plasmids HCMV-κ-C21/L1 and HCMV-γ1-C21/H1 (depicted in FIG. 1) wherein the Hind III-BamHI fragment coding for the reshaped human light or heavy chain variable region is joined to a DNA coding for human κ and γ1 constant regions, respectively. Both plasmids comprise the origin of Simian Virus 40 (SV40), the HCMV enhancer domain, the HCMV promoter, and the ampicillin selectable gene (Kettleborough et al., 1991, supra).

Reshaped human C21 $V_L$ region versions C21-L2 and C21-L3 are generated by oligonucleotide-directed mutagenesis, making use of recombination events which occur during PCR reactions (Mullis, K., Faloona, F., Scharf, S., Saiki, R., Horn, G. and Ehrlich, H., 1986, Cold Spring Harbour Symp., 51:263 and Yolov, A. A. and Shabarova, Z. A., 1990, Nucl. Acids Res., 18:3983). Oligonucleotide primers C21–5'(SEQ ID NO. 31), L/D60SL (SE:Q ID NO. 35), L/D60S-SL (SEQ ID NO. 36) (for C21-L2), RSP (SEQ ID NO. 34), L/E1 D-V3$_L$ (SEQ ID NO. 37), L/E1D-V3L-SL (SEQ ID NO. 38), (for C21L3) and C21-L3 (SEQ ID NO. 33) (for C21-L2 L3) are synthesized in order to generate by PCR amplification two DNA fragments, for each of the two light chain V-region versions. Except for the terminal oligonucleotide primers (C21–5', RSP and C21-L3') oligonucleotides incorporate sequences needed for the desired codon changes. Except for primer pair RSP and LE1D-V3$_L$, about 50 pmol each of the appropriate primer pair is combined with ca. 10 ng of a Xho I-Not I fragment from KS+C21/L1, 3 units of VentTM DNA polymerase and 25 PCR amplification cycles are used (60° C./25 s, 72° C./40 s and 93° C./25 s). For primer pair RSP and L/E1D-V3$_L$, ca. 150 ng of KS+C21/L1 plasmid DNA is used as a template and the desired DNA fragment PCR amplified using 35 cycles (40° C./30 s, 72° C./1 min and 93° C.130 s). The products of these reactions, purified by agarose gel electrophoresis, are first combined, and ca. 5–30 ng of each DNA fragment extended with 5 units of VentTM DNA polymerase (95° C./1 min, 5°° C./2min and 72° C./4 min). Terminal oligonucleotide primers C21–5' and C21-L3' are then added and the combined full-length DNA fragment PCR amplified using 25 cycles (95° C./1 min, 50° C./2 min and 72° C./2 min). amplified DNAs for C21-L2 and C21-L3 are then subcloned into pBluescript KS II M13+(Stratagene) after digestion using DNA restriction endonucleases Hind III and BamHI, and sequenced. Correct sequences are then transferred into the HCMV-γ1-expression vector as described above.

Reshaped human C21 $V_H$ region versions C21-H3, C21-Hayl and C21-Hay3 are generated in a similar manner as described for C21-L1 and C21-L2. To obtain these C21 $V_H$ region versions, oligonucleotide primers C21–5', H/R38K-A40R-L (SEQ ID NO. 39), H/R38K-A40R-SL ((SEQ ID NO. 40), H/R67K-L (SEQ ID NO. 41), H/R67K-SL (SEQ ID NO. 42), H/R87T-L (SEQ ID NO. 43), H/R87T-S (SEQ ID NO. 44), HayFR2 (SEQ ID NO. 45), HayFR2-S (SEQ ID NO. 47), HayFR3 (SEQ ID NO. 48), HayFR3S (SEQ ID NO. 49) and C21-H3' are used to PCR amplify, using C21-H1 (for C21-H3 and C21-Hay1) or C21-H3 (for C21-Hay3) as DNA templates, double-stranded DNA fragments containing the desired codon changes for the different reshaped human C21 $V_H$ versions. Corresponding, agarose gel-purified fragments are then assembled by PCR recombination to yield the full-length DNA-fragments, as described above. After digestion with DNA restriction endonucleases Hind III and BamHI, followed by cloning into pBluescript KS II M13+(Stratagene) as described above, plasmid clones are checked for the correct sequence before being cloned into the HCMV-γ1-expression vector.

EXAMPLE 4

Transient Expression of Recombinant Plasmids in COS Cells

COS cells are electroporated using 10 μg of the HCMV expression vectors bearing the genes coding for the reshaped human C21 heavy and light chains. 10 μg of H- and L-chain expression plasmids are added to 0.8ml of a $1 \times 10^7$ cells/ml suspension of COS cells in PBS/o (PBS lacking $Ca^{2+}$ and $Mg^{2+}$ supplied by GIBCO-BRL, Basel, Switzerland; cat.no. 041–04190M). A Bio-Rad Gene Pulser is then used to deliver to the suspended cells a pulse of 1900 V at a capacitance of 25 μF. The cells are allowed to recover for 10 min before plating into 10 ml DMEM containing 5% v/v gammaglobulin-free and heat-inactivated fetal calf serum (GIBCO-BRL, Basel, Switzerland; cat. no. 063–06510 H). After 72 h incubation, the meclium is collected, centrifuged to remove cells and cellular debris. The COS cell supernatant is then filtered through a 0.45 μm membrane and analysed for the presence of assembled antibody of human γ1/κ isotype by ELISA. The humanized antibodies are further purified by protein A affinity chromatography.

EXAMPLE 5

ELISA Assay for Human IgG/κ Production 96-well microtiter plates (Nunc MaxiSorb, cat. No. 439454) are coated overnight with 50pl of a 1:1000 dilution of goat anti-human IgG (Fc specific; Dianova, #

109–005–098) in PBS/o, pH 7.2. After this and all subsequent steps, plates are washed 3× with 200 μl PBST (PBS/o pH 7.2 containing 0.05% Tween-20). Free binding sites are blocked for 1 h at 37° C. with 100 μl RIA-buffer (1% bovine serum albumin in PBST). 50 μl of samples, and dilutions thereof in RIA-buffer, are added and the mixtures incubated for 1 h at 37°. Highly purified recombinant human antibody F5-444 (human γ1/κ isotype, European Patent Application No. 498767) serves as a standard. 50 μl of a 1:1000 dilution of affinity-purified goat anti-human κ-light chain antiserum conjugated with horseradish peroxidase (Sigma, Buchs, Switzerland; cat. no. A-7164) in RIA-buffer is then applied and incubated for 1 h at 37° C. 100 μl of ABTS (2,2'-Aziriobis(3-ethylbenzthiazoline-6-sulfonic acid)) substrate solution (BioRad, Glattbrugg, Switzerland; #172-1064) used for development. After an appropriate incubation time the enzymic reaction is stopped using an equal volume (100 μl) of 2% (w/v) oxalic acid. The absorption at 415 nm is used for quantitation of bound and fully assembled human antibody.

EXAMPLE 6

Protein A Purification of Humanized Antibodies from COS Cell Supernatants

Transiently-expressed humanized antibodies are purified by affinity chromatography on a 1 ml Prosep A column (Bioprocessing Ltd, Durham, England) packed into a HR 5/5 FPLC column (Pharmacia, Uppsala, Sweden). The column is run at constant flow rate of 2ml/min on an FPLC system (Pharmacia, Uppsala, Sweden) and protein eluting from the column is detected in a flow cell by u.v.-absorbance at 280nm. The column is prepared by washing with 10 column volumes of PBS/o pH 8.0 (20 mM NaPhosphate, 150 mM NaCl), pre-elution with 10 column volumes of 100 mM sodium citrate buffer pH 3.0 and re-equilibration with 10 column volumes of PBS/o pH 8.0. COS cell supernatants (20–50ml), clarified by filtration through a 0.45 μm membrane, are loaded directly on to the column with a peristaltic pump. The column is then washed with PBS/o pH 8.0 until the u.v.-absorbance returns to baseline. Bovine IgG is then eluted by washing with 100 mM sodium citrate buffer pH 5.0 until the baseline returns to zero. Finally humanized antibodies are eluted using 100 mM sodium citrate buffer pH 3.0 and the eluates immediately adjusted to pH 7.0 by addition of 1 M Trizma-Base (Sigma, Buchs, Switzerland). The purity of the humanized antibodies is analysed by SDS-Polyacrylamide gel electrophoresis using Coomassie blue staining (Laemmli, U. K., 1970, Nature, 227:680–685). For biosensor analysis the neutralized Protein A eluates are concentrated in a Centricon-10 microconcentrator (Amicon) and the buffer changed to PBS/o pH 7.2. Depending on the purity of the antibody preparation, the protein concentration is quantified either by u.v.-absorption at 280 nm or by human γ/κ ELISA using a known, purified recombinant chimeric antibody F5-444 of matched isotype as a standard.

EXAMPLE 7

Analysis of the Avidity and Specificity of Mouse and Reshaped Human C21 Antibodies by Biospecific Interaction Analysis (BIA)

The avidity and specificity of the different combinations of reshaped human C21 variable light and heavy chains are analyzed using real-time biospecific interaction analysis (J önsson, U., Fägerstam, L., Ivarsson, B., Johnsson, B., Karlsson, R., Lundh, K., Löfas, S., Persson, B., Roos, H., R önnberg, I., Sjölander, S., Stenberg, E., Stahlberg, R., Urbaniczky, C., Östlin, H. and Malmqvist, M., 1991, BioTechniques, 11:620–627). All experiments are performed on the BlAcore™ system (Pharmacia Biosensor AB, Uppsala, Sweden) using CM5 sensor chips. As capture antibodies, ca. 11,000 RU (11 ng/mm2) of polyclonal rabbit anti-mouse IgG1 (Pharmacia Biosensor AB, Uppsala, Sweden, cat.no. BR-1000–55) or rabbit anti-human IgG (obtained from Pharmacia Biosensor AB) are immobilized on to the sensor chip surface using their amino groups and EDC/NHS chemistry essentially as described previously (J önsson, U. et al., 1991, supra). Four experimental cycles are performed for each antibody to determine the association rate of binding to human IgE. Each cycle consists of binding of a constant amount of test antibody to the respective catching antibody, followed by the interaction of this test antibody with a fixed concentration of antigen (human IgE; monoclonal antibody SE44; 3.125, 6.25, 12.5 and 25 nM) followed by a final regeneration of the surface using 40 mM HCl. Experimental details are as follows:

[1] The flowrate is 5 μl per min;
[2] HBS (10 mM Hepes, 3.4 mM EDTA, 150 mM NaCl, 0.05% BIAsurfactant, pH 7.4) is used as running buffer;
[3] Test antibodies (in PBS/o pH 7.2) are diluted in HBS to a final concentration of 5–10 μg/ml, and bound to the capture antibody to obtain 1300–2200 RU (1.3–2.2 ng/mm2) of bound test antibody;
[4] Human monoclonal IgE (SE44) is passed over the bound test antibody for 9 min;
[5] 4 μl 40 mM HCl is used to remove antibody-antigen complexes and prepare the surface for the next cycle;
[6] The assay temperature is 25° C.

The association constants of the antibody-antigen interactions are then calculated using computer programs implemented in the Biocore™ system.

For the determination of dissociation rate constants a similar protocol is used, except that a dissociation phase is included. Assay conditions are as described above. Test antibodies are first bound to the sensor chip surface via immobilised catching antibodies. IgE (SE44) at the highest concentration (25 nM) is allowed to bind to the antibody. Following binding HBS buffer is passed over the sensor chip surface at a constant flow rate of 5 μl/min and the decrease in resonance signal monitored over a period of 15 to 25 min. The sensor chip is finally regenerated by washing with 4 μl of 40 mM HCl solution. Since the dissociation of antibody:IgE complexes is a first-order reaction the linear parts of the sensorgramms are taken to calculate the dissociation rate constants using computer progammes implemented in the BIACORE™ system.

The kinetic constants $k_{ass}$ (velocity constant of the antibody-antigen association) and $k_{diss}$ (velocity constant of the dissociation of the antibody-antigen complex) and avidity (represented by the equilibrium constant $K_{aff}$) of reshaped human C21 antibodies are summarized in Table 1.

Table 1: Kinetic constants and avidity of reshaped human C21 antibodies. For $K_{ass}$ the number of independent experiments is given in brackets (n); each $K_{diss}$ is determined in two independent experiments.

| antibody | $k_{ass} \times 10^5$ M$^{-1}$s$^{-1}$ | $k_{diss} \times 10^{-5}$ s$^{-1}$ | $K_{aff} \times 10^{10}$ M$^{-1}$ |
|---|---|---|---|
| TES-C21 | 2.4 ± 0.3 (6) | 2.6 ± 0.0 | 0.92 ± 0.12 |
| C21-H1/L1 | 2.6 ± 0.1 (3) | 3.0 ± 1.1 | 0.87 ± 0.32 |

-continued

| antibody | $k_{ass} \times 10^5 \, M^{-1}s^{-1}$ | $k_{diss} \times 10^{-5}s^{-1}$ | $K_{aff} \times 10^{10} \, M^{-1}$ |
|---|---|---|---|
| C21-H1/L2 | 2.8 ± 0.1 (3) | 5.7 ± 0.2 | 0.49 ± 0.02 |
| C21-HI/L3 | 2.9 ± 0.4 (3) | 6.2 ± 1.0 | 0.47 ± 0.10 |
| C21-H3/L1 | 2.5 ± 0.3 (3) | 1.9 ± 0.6 | 1.32 ± 0.44 |
| C21-H3/L2 | 2.5 ± 0.3 (4) | 4.4 ± 0.7 | 0.57 ± 0.11 |
| C21-H3/L3 | 2.6 ± 0.5 (3) | 3.5 ± 0.2 | 0.74 ± 0.15 |
| C21-Hay3/L1 | 2.5 ± 0.3 (3) | 4.1 ± 0.6 | 0.61 ± 0.12 |
| C21-Hay3/L2 | 2.5 ± 0.3 (3) | 3.1 ± 0.6 | 0.81 ± 0.18 |
| C21-Hay3/L3 | 2.6 ± 0.3 (3) | 15.9 ± 1.8 | 0.16 ± 0.03 |

All of these reshaped human C-21 antibodies have quite similar rates of association. The reductions in the avidity of binding are caused mainly by higher rates of dissociation. Different versions of reshaped human C21 light chains are analyzed for the importance of positions 1 and 3 at the amino terminus. Good binding to antigen is obtained when the amino acids at these positions are the same as those present in the C21 light chain. Using the entire human KAF FRI decreases the binding regardless of the heavy chain partner.

The reshaped human C21 antibodies are also tested for binding to all isotypes of human immunoglobulins by biospecific interaction analysis. First, the test antibodies are separately bound to immobilized capture antibodies on sensor chips as described above. Cross-reactivity of these immobilized rabbit anti-human IgG and rabbit anti-mouse IgGl antibodies is then blocked using chimeric anti-CEA antibody 10 μg/ml ReK.41 for 5 min (human γ1/κ, European Patent Application No. 323806), before 5 μg/ml of human immunoglobulins of all isotypes IgM, IgD, IgA1, IgA2, IgG4, IgG3, IgG2, IgG1 and IgE (SE44) are passed successively over this pretreated surface for 5 min each. Finally, the surface is regenerated with 40 mM HCl. Flowrates, temperature and other conditions are the same as described above. Sensorgramms are recorded with the BIAcore™ system. The reshaped human C21 antibodies are specific for human IgE isotype.

EXAMPLE 8

Making Permanent Cell Lines

Plasmid DNAs of reshaped TESC-21 human CMV H- and L- chain expression vectors for transfection are purified by centrifugation to equilibrium in caesium chloride gradients two times. The recombinant immunoglobulin genes are introduced into mouse myeloma NSO cells by electroporation with the use of a Gene Pulser apparatus (BioRad, Richmond, Calif.). NSO cells (2 to $3\times10^7$) are washed with phosphate-buffered saline (PBS), and resuspended in 0.8 ml of PBS containing 10 μg each of BspCI-linearized H- and L-chain plasmid DNAs Electroporation is performed at an electric field of 210 V and a capacitance of 960 μFD. Cells recovered are diluted in Protein-Free Hybridoma Medium (PFHM, Gibco) containing 2% FBS (fetal bovine serum), and plated out in 96-well microtiter plates at 104 cells per well. After 48 h incubation the transfectants are selected in PFHM containing 0.7 mg/ml G418 (Gibco) and 2% FCS (foetal calf serum). After 2 weeks, wells containing drug resistant colonies are screened for the production of human IgG by ELISA. An ELISA is developed for the quantitation of the recombinant human IgG/kappa antibody expressed in the culture supernatant. Immulon 2 (Dynatech Labs) 96-well plates are coated overnight with 100 μl of 0.5 μg/ml goat anti-human kappa antibody (Southern Biotech) in PBS at room temperature. Wells are then blocked with Blotto (5% dry milk powder in PBS) for 1 h and washed with PBS containing 0.05% Tween-20 (PBST). Culture supernatant (50 μl) is added to the coated wells and incubated for 1 h. After washing with PBST, 100 μl of horseradish peroxidase-conjugated goat anti-human IgG(Fc) antibody (Jackson lmmunoResearch Lab), diluted at 1/50,000 in Blotto, is added to each well, and the plate is incubated for 1 hour. Peroxidase substrate solution containing 0.1% 3',3", 5',5"-tetramethyl benzidine (Sigma) and 0.003% Hydrogen peroxide (Sigma) is added at 100 μl per well and incubated at room temperature for 0.5 hour. The reaction is stopped by the addition of 50 μl of 2 M sulphuric acid and the O.D. of the reaction mixture in each well is read at 450 nm with a Dynatech MR5000 μlate reader. Reshaped TESC-21 human CMV expression plasmids, H1, H3, L1, and L3, are used to transfect NSO cells in four combinations: H3L1, H3L3, H1L1, and H1L3. A total of 142, 122, 68, and 64 wells of H3Ll, H3L3, H1L1, and H1L3, respectively, give O.D. readings of greater than 0.05 with background reading below 0.01. For each combination, one cell line is chosen based on IgG secretion levels: EH31.8, secreting the H3L1 antibody; EH33.16, secreting the H3L3 antibody; EH11.13, secreting the H1L1 antibody; and EH13.5, secreting the H1L3 antibody.

Deposition data

The following cell lines have been deposited with the American Type Culture Collection (ATCC), 12301 Parklawn Drive, Rockville, Md. 20852, U.S.A., on Sep. 23, 1993 (accession nos. given in brackets).

Cell line EH31.8 producing reshaped human antibody H3Ll (HB 11130)

Cell line EH11.13 producing reshaped human antibody H1L1 (HB 11132)

Cell line TES-C21 producing murine monoclonal antibody TES-C21 (HB 11133)

Cell line EH33.16 producing reshaped antibody H3L3 (HB 11131)

Cell line EH13.5 producing reshaped antibody H1L3 (HB 11134).

We claim:

1. A process for the preparation of an antibody, a direct equivalent or a derivative thereof, said antibody specific for IgE comprising an antibody comprising an antigen binding site comprising, in sequence, the hypervariable regions CDR1, CDR2 and CDR3 and a human framework; said CDR1 having the amino acid sequence of SEQ ID NO 50, said CDR2 having the amino acid sequence of SEQ ID NO 51, said CDR3 having the amino acid sequence of SEQ ID NO 52, said antibody having an antigen binding affinity at least 90% of that of the murine CDR-donor antibody TES-C21, comprising culturing a suitable host encoding DNA capable of expressing said antibody and, isolating said protein and converting said isolated protein into a derivative, wherein direct equivalents comprise hypervariable regions CDR1, CDR2 and CDR3 and derivatives are selected from the group consisting of radioactively labeled antibodies and antibodies conjugated with an enzyme, a fluorescent marker, a chemiluminescent marker, a cytotoxic substance, a cytostatic substance, a metal chelate, a non-antibody protein, or a non-proteinaceous molecule.

2. A DNA construct encoding a heavy chain or a fragment thereof comprising a) a first part which encodes a variable domain comprising alternatively FRs and CDRs, said FRs being human and said CDRs being in sequence $CDR1_H$, $CDR2_H$, and $CDR3_H$, the amino acid sequences of which are $CDR1_H$ having the amino acid sequence of SEQ ID NO 50, said $CDR2_H$ having the amino acid sequence of SEQ ID NO 51, and said $CDR3_H$ having the amino acid sequence of SEQ ID NO 52, and b) a second part encoding a human heavy chain constant region or fragment thereof.

3. A hybrid vector comprising a DNA construct according to claim 2.

4. A host cell transformed with a hybrid vector according to claim 3.

5. A host cell according to claim 4 which is cell line EH 11.13, wherein said EH11.13 is ATCC Accession No. HB 11132.

6. A host cell according to claim 4 which is cell line EH 31.8, wherein said EH11.13 is ATCC Accession No. HB 11130.

7. The process of claim 1 further comprising converting said isolated antibody into a derivative, wherein said derivative is selected from the group consisting of radioactively labeled antibodies and conjugated antibodies, wherein the conjugated antibodies are conjugated to an enzyme, a fluorescent marker, a chemiluminescent marker, a cytotoxic substance, a cytostatic substance, a metal chelate, a non-antibody protein that is avidin, or a non-proteinaceous molecule that is biotin.

8. A DNA construct encoding a light chain or a fragment thereof comprising a) a first part which encodes a variable domain comprising alternatively FRs and CDRs, said FRs being human and said CDRs being in sequence $CDR1_L$, $CDR2_L$, and $CDR3_L$, the amino acid sequences of which are $CDR1_L$ having the amino acid sequence of SEQ ID NO 53, said $CDR2_L$ having the amino acid sequence of SEQ ID NO 54, and said $CDR3_L$ having the amino acid sequence of SEQ ID NO 55, and, b) a second part encoding a human heavy chain constant region or fragment thereof.

9. A hybrid vector comprising a DNA construct according to claim 8.

10. A host cell transformed with a hybrid vector according to claim 9.

* * * * *